US009750906B2

(12) United States Patent
Martin et al.

(10) Patent No.: US 9,750,906 B2
(45) Date of Patent: *Sep. 5, 2017

(54) METHODS, SYSTEMS AND APPARATUS FOR PACED BREATHING

(71) Applicant: ResMed Limited, Bella Vista, New South Wales (AU)

(72) Inventors: Dion Charles Chewe Martin, Concord (AU); David John Bassin, Coogee (AU)

(73) Assignee: ResMed Limited (AU)

( * ) Notice: Subject to any disclaimer, the term of this patent is extended or adjusted under 35 U.S.C. 154(b) by 240 days.

This patent is subject to a terminal disclaimer.

(21) Appl. No.: 14/334,240

(22) Filed: Jul. 17, 2014

(65) Prior Publication Data

US 2014/0326241 A1    Nov. 6, 2014

Related U.S. Application Data

(63) Continuation of application No. 12/585,572, filed on Sep. 17, 2009, now Pat. No. 8,844,527, which is a
(Continued)

(51) Int. Cl.
  *A61M 16/00*    (2006.01)
  *A61M 16/20*    (2006.01)

(52) U.S. Cl.
  CPC .... *A61M 16/0003* (2014.02); *A61M 16/0051* (2013.01); *A61M 16/0069* (2014.02);
(Continued)

(58) Field of Classification Search
  CPC .............. A61M 16/00; A61M 16/0051; A61M 16/0066; A61M 16/10; A61M 2016/0015;
(Continued)

(56) References Cited

U.S. PATENT DOCUMENTS

| 8,844,527 B2 * | 9/2014 | Martin .............. A61M 16/0051 128/204.18 |
| 2001/0004893 A1 * | 6/2001 | Biondi .................. A61M 16/00 128/204.18 |

(Continued)

FOREIGN PATENT DOCUMENTS

| FR | 2866812 | 9/2005 |
| JP | 2006-207508 | 8/2006 |

(Continued)

Primary Examiner — Valerie L Woodward
(74) Attorney, Agent, or Firm — Lerner, David, Littenberg, Krumholz & Mentlik, LLP

(57) ABSTRACT

Methods, systems and/or apparatus for slowing a patient's breathing by using positive pressure therapy. In certain embodiments, a current interim breathing rate target is set, and periodically the magnitude of a variable pressure waveform that is scaled to the current interim breathing rate target is increased if the patient's breathing rate is greater than the interim breathing rate target in order to lengthen the patient's breath duration. The magnitude of the pressure increase may be a function of the difference between the interim breathing rate target and the patient's breathing rate. The interim breathing rate target may be periodically reduced in response to the patient's breathing rate slowing down toward the current interim breathing rate target. The variable pressure waveform cycles from an inhalation phase to an exhalation phase when the patient airflow decreases to a cycle threshold, the cycle threshold being a function of flow versus time within a breath and generally increasing with time. Different interim breathing rate targets have different cycle threshold functions, and the cycle threshold functions allow easier cycling as the interim breathing rate targets decrease. Similarly, the variable pressure waveform triggers from an exhalation phase to an inhalation phase when the patient airflow increases to a trigger threshold, the trigger threshold being a function of flow versus time within a breath and
(Continued)

generally decreasing with time. Different interim breathing rate targets have different trigger threshold functions, and the trigger threshold functions allow easier triggering as the interim breathing rate targets decrease.

60 Claims, 9 Drawing Sheets

Related U.S. Application Data continuation-in-part of application No. 12/422,411, filed on Apr. 13, 2009, now abandoned.

(60) Provisional application No. 61/045,161, filed on Apr. 15, 2008.

(52) U.S. Cl.
CPC ... *A61M 16/204* (2014.02); *A61M 2016/0018* (2013.01); *A61M 2016/0036* (2013.01); *A61M 2205/502* (2013.01); *A61M 2230/06* (2013.01); *A61M 2230/205* (2013.01); *A61M 2230/42* (2013.01)

(58) Field of Classification Search
CPC .. A61M 2205/3331; A61M 2205/3334; A61M 2230/42; A61M 2230/005
See application file for complete search history.

(56) References Cited

U.S. PATENT DOCUMENTS

| | | | | |
|---|---|---|---|---|
| 2004/0231670 | A1* | 11/2004 | Bassin | A61M 16/00 128/204.18 |
| 2006/0011195 | A1* | 1/2006 | Zarychta | A61M 16/00 128/200.14 |
| 2008/0035147 | A1* | 2/2008 | Kirby | A61M 16/0051 128/204.21 |

FOREIGN PATENT DOCUMENTS

| | | |
|---|---|---|
| WO | WO 80/01501 | 7/1980 |
| WO | WO 00/38771 | 7/2000 |
| WO | WO 2005/097244 | 10/2005 |
| WO | WO 2008/021222 | 2/2008 |

* cited by examiner

METHODS, SYSTEMS AND APPARATUS FOR PACED BREATHING

CROSS REFERENCE TO RELATED APPLICATIONS

This application is a continuation of U.S. application Ser. No. 12/585,572, filed Sep. 17, 2009, which is a continuation-in-part of U.S. application Ser. No. 12/422,411, filed Apr. 13, 2009, which claims the benefit of U.S. Provisional Application No. 61/045,161 filed on Apr. 15, 2008. These applications, in their entirety, are each incorporated herein by reference.

FIELD OF THE INVENTION

The disclosure relates to methods, systems and apparatus for paced breathing.

BACKGROUND OF THE INVENTION

Hypertension and cardiac failure are both diseases that cannot always be controlled with current medications. With hypertension, any decrease in blood pressure (particularly pulse pressure) is beneficial. Hypertensive and cardiac failure patients possess heightened sympathetic tone (higher basal activity) and chemoreflex (hypoxic, relating to deficiencies of oxygen) response (a reflex initiated by the stimulation of chemoreceptors, which are specialized cells for detecting chemical substances and relaying that information centrally in the nervous system). Other conditions are also associated with heightened sympathetic tone, which can impart extra load on the heart and other organs. Arterial stiffness, directly related to sympathetic activation and blood pressure, is attracting abundant clinical attention presently, and methods which directly reduce it are now a goal in themselves.

Slow breathing improves arterial baroreflex sensitivity and decreases blood pressure in essential hypertension, which continuous positive airway pressure (CPAP) may assist by avoiding nightly repetitive desaturation and arousal. For example, in certain situations slowed breathing, at 6 breaths per minute, has been shown to be beneficial. Slowed breath rate can independently improve sympathovagal balance, of potential benefit to the general population interested in maximizing cardiovascular health or minimizing stress. ("Sympathovagal balance" refers to the autonomic state resulting from both sympathetic and parasympathetic influences; the autonomic nervous system directs all activities of the body that occur without a person's conscious control, such as breathing and food digestion. Typically, it has two parts: the sympathetic division, which is most active in times of stress, and the parasympathetic division, which controls maintenance activities and helps conserve the body's energy.)

Severe chronic obstructive pulmonary disease (COPD, a term referring to two lung diseases, chronic bronchitis and emphysema) is a condition of airway flow limitation, associated with hypercapnia (a condition in which there is too much $CO_2$ in the blood) and hypoxaemia (a condition in which there is too little $O_2$ in the blood), increased respiratory muscle loading, diminished exercise capacity, elevated respiratory rate, etc. Noninvasive positive pressure ventilation (NPPV, delivery of ventilatory support using a mechanical ventilator connected to a mask or mouthpiece) sessions promoting deep and slowed breathing have been shown to be beneficial, possibly due to a lowered effective respiratory impedance, and a deep slow pattern of breathing has been maintained by patients between sessions.

Therapies exist to help train a patient to consciously breathe slowly using acoustic feedback/training. See, for example, the system known as RESPeRATE (http://www.resperate.com/). See also PCT Publication Number WO 2008/021222, which discloses use of a CPAP machine to reduce a patient's breathing rate.

Thus a paced-breathing systems, methods and/or apparatus that achieves sustained target breath rate in a comfortable and/or tolerated fashion are needed. The therapy may be delivered as daytime sessions of prescribed duration and/or as a nocturnal therapy. The therapy goal is to modify breath rate by delivering mechanical ventilation optimized to achieve a rate target, but sympathetic to the response of the patient such that the therapy is well tolerated. In certain embodiments, the goal is to lower rate to a value optimized to suit the patient and/or the pathology. In certain embodiments, the goal may be to reach an optimal rate, possibly higher than the patient's spontaneous rate.

SUMMARY OF THE INVENTION

Certain embodiments of the present disclosure are directed to slowing a patient's breathing during sleep and/or during awake sessions by using positive pressure therapy.

Certain embodiments of the disclosure are directed to providing for a patient improved cardiovascular health without and/or minimal side effects.

Certain embodiments of the disclosure are directed to applying therapy during sleep (rather than during specific periods of the day) so that a longer treatment session at greater personal convenience is achieved.

Certain embodiments of the disclosure are directed to achieving the foregoing while resolving at the same time certain patient sleep disordered breathing (SDB).

In certain embodiments, following a settling period during sleep onset, during which breathing is largely spontaneously triggered, a variable pressure waveform is applied to the patient's airway. An interim breathing rate target may be set, and periodically the magnitude of the pressure waveform is changed (for example increased) when the patient's breathing rate is greater than the interim breathing rate target in order to lengthen the patient's breath duration. Periodically, in response to the patient's breathing rate slowing down toward the current interim breathing rate target, the interim breathing rate target is reduced. The reduction may follow a predetermined path, but the reduction may be paused if, for example, the patient's breathing rate is excessively high for the current interim breathing rate target.

In certain embodiments, the variable pressure waveform cycles from an inhalation phase to an exhalation phase when the patient airflow decreases to a cycle threshold, the cycle threshold being a function of flow versus time within a breath and generally increasing with time. Different interim breathing rate targets have different cycle threshold functions, and the cycle threshold functions allow easier cycling as the interim breathing rate targets decrease. Similarly, the variable pressure waveform triggers from an exhalation phase to an inhalation phase when the patient airflow increases to a trigger threshold, the trigger threshold being a function of flow versus time within a breath and generally decreasing with time. Different interim breathing rate targets have different trigger threshold functions, and the trigger threshold functions allow easier triggering as the interim breathing rate targets decrease.

In certain embodiments, pressure adjustments are not always upward. The magnitude of the pressure waveform is decreased if the patient's breathing rate is less than the interim breathing rate target. In general, in certain embodiments, the magnitude of a pressure increase or decrease is a function of the difference between the interim breathing rate target and the patient's breathing rate. The duration of the pressure waveform may be adjusted in accordance with the current interim breathing rate target.

Another way of looking at the certain embodiments of the present disclosure is to view it as the use of a ventilator coupled to a patient's airway, where an interim breathing rate target is set, the pressure support supplied to the patient's airway from the ventilator during patient breaths (not necessarily all breaths) is increased if the patient's breathing rate is greater than the interim breathing rate target in order to lengthen the patient's breath duration, and the interim breathing rate target is reduced in response to the patient's breathing rate slowing down toward the interim breathing rate target. The pressure-support increase and interim breathing rate target reduction steps are interrupted if the patient exhibits opposition to breath duration lengthening, but otherwise the air increase and interim breathing rate target reduction steps are controlled to take place over a period of minutes to hours in the absence of patient opposition.

Since brief (15 minute) sessions of slow breathing while awake offer a beneficial reduction in blood pressure or sympathetic activation, the same principle (slowed breathing) successfully achieved during sleep via a positive pressure therapy offers greater benefit (longer therapy time) while simultaneously avoiding obstructive sleep apnea (OSA) and respiratory effort related arousal (RERA) activity, and it is more time efficient for the patient. Over time, the patient's spontaneous rate is reduced as the chemoreflex normalizes, but in advance of that occurring, the patient enjoys hours at the slower (therapeutic) rate during sleep, compared with minutes with the conscious method. For the case of COPD, whether the paced breathing system is used during daytime sessions or nocturnally while asleep, by algorithmically lowering rate, compared to traditional NPPV, the paced breathing system offers clinical convenience (reduced, little, or no supervision necessary) and it optimizes outcomes. In certain embodiments, the patient may also achieve these benefits if awake and/or asleep.

In certain embodiments, the goal is to entrain the patient to an ideal breath rate, e.g., lowered to 6 breaths per minute or as low as the patient will tolerate. In certain embodiments, the goal is to entrain the patient to a breath rate, e.g., lowered to approximately 12, 11, 10, 9, 8, 7, 6, 5, 4, or 3 breaths per minute over a desired time period. This time period may be 10%, 20%, 30%, 40%, 50%, 60%, 70%, 80% or 90% of the time that the patients is using the method, system, and/or apparatus. This low rate is partially achieved through maximizing, or substantially maximizing, inspiratory duration through elevated tidal volume, but much of the rate retardation is achieved by sustaining expiration and promoting an end-expiratory pause.

In certain embodiments, a factor is slow pressurization and de-pressurization. Fast pressurization (inspiratory positive airway pressure—IPAP) is known to hasten inspiration, to be avoided, while total occlusion of the patient airway during inspiration tends to sustain inspiratory effort. A slow pressurization will slow down inspiration, or at least not hasten it. Similarly, once cycling occurs, the de-pressurization is controlled and tapered such that it reaches the target EPAP (end positive airway pressure) just prior to the target inspiratory time, again to slow breathing. (For patients with obstructive airway disease, suffering slow lung inflation/deflation already, and also suffering dyspnoea, a slow pressurization and recoil may be in certain situations disadvantageous, and a squarer waveform may be selected based on preference or application.) Once the patient's breathing rate is reduced to an interim target rate, the basic mechanism of certain embodiments is to increase the pressure slightly; for minute volume (volume of air which can be inhaled or exhaled from a person's lungs in one minute) to remain the same, the patient tends to lengthen the breath duration. The target rate is then reduced again, hopefully followed by another lengthening of the patient's breath as he/she maintains his/her minute volume.

In certain embodiments, the trigger scheme permits the patient to breathe at his/her preferred spontaneous rate, but aims to encourage the optimal, or substantially optimal, rate by having a trigger threshold that initially is insensitive, or substantially insensitive, and which becomes most sensitive, or more sensitive, only as the ideal, or desired, breath period is approached. And for the interim target rate, following expiratory cycling there is an initial refractory period where triggering is insensitive, or substantially insensitive, followed by progressive sensitization, slowly approaching a more typical trigger threshold by the desired (for the current interim target rate) end-expiratory period (e.g., sensitivity progressively increasing from, for example, 20 L/min to 5-7 L/min). Similarly, the cycling scheme that is employed encourages cycling at the target inspiratory duration through progressive change in cycle threshold from highly insensitive to highly sensitive by the target inspiratory time. In certain aspects, the cycling scheme that is employed encourages cycling at the target inspiratory duration through progressive change in cycle threshold from insensitive to sensitive by the target inspiratory time.

Although not shown, in certain embodiments it is contemplated that monitoring of the patient can include at least one of, or combinations thereof of respiratory parameters and customized pulse oximetry, and capturing of instantaneous heart rate suitable for heart rate variability (HRV) or similar analysis. Also, daytime sessions can be augmented via biofeedback for inspiratory/expiratory timing, e.g., acoustic methods such as RESPeRATE mentioned herein or discernible pneumatic fluctuations communicated via the patient's CPAP mask, visual cues, or combinations thereof.

In certain embodiments, the disclosed methods, systems, and/or apparatus operate so as to synchronize to the patient's breathing rate rather than to operate in accordance with the interim breathing rate target. In certain aspects, the disclosed methods, systems, and/or apparatus are not synchronized to an interim breathing rate target In certain aspects, the ventilator synchronizes to the patient's breathing, by detecting a change in the patient's breathing phase. An attempt is not made to lower the patient's breathing rate by slowing down the ventilator in the hope that the patient will 'synchronize' to the ventilator. The ventilator instead increases the pressure support to the patient in the hope that the patient will slow down his breathing rate, while the ventilator remaining synchronized to the patient's breathing rate.

In certain embodiments, even though the ventilator operation is synchronized to phase changes in patient breathing, the pressure waveform template changes its scale to that of a new, longer interim target breath period. In other words, the ventilator supplies a pressure waveform whose duration corresponds with a longer breath period, even though a patient phase change will abort a ventilator phase in progress. This conditions the patient to breathe more slowly without attempting to force a rate change; the ventilator attempts to lead the patient to a slower rate.

In certain embodiments, the pressure is continuously adjusted. Not only is a continuously variable pressure template used for each breathing cycle, but the amplitude of the waveform is adjusted from cycle to cycle. In certain embodiments, the pressure may be continuously, substantially continuously and/or capable of being continuously adjusted. In certain aspects, the pressure template used for breathing cycles may be continuously, substantially continuously and/or capable of being continuously adjusted. In certain aspects the amplitude of the waveform may be continuously, substantially continuously and/or capable of being continuously adjusted from cycle to cycle. In certain aspects, the pressure, the pressure template, the wave form or combinations thereof may be continuously, substantially continuously and/or capable of being continuously adjusted.

In certain embodiments, the target rate is changed not only as a function of recent breathing periods of the patient, but also in accordance with a predetermined gradient that may require, hours days or even weeks before the desired rate is achieved.

In certain embodiments, each phase length is independently operated upon. In certain embodiments, a substantial number of the phase lengths are independently operated upon.

In certain embodiments, the thresholds for determining whether a change in breathing phase should be effected continuously change not only within a breath, but also with the current breathing rate. In certain embodiments, the thresholds for determining whether a change in breathing phase should be effected continuously, substantially continuously or is capable of being continuously changed not only within a breath, but also with the current breathing rate.

Certain embodiments are to methods and/or systems for slowing a patient's breathing during sleep by using positive pressure therapy comprising the steps of applying a variable pressure waveform to the patient's airway, setting a current interim breathing rate target, periodically increasing the magnitude of the pressure waveform when the patient's breathing rate is greater than the interim breathing rate target in order to lengthen the patient's breath duration, and periodically reducing the interim breathing rate target in response to the patient's breathing rate slowing down toward the current interim breathing rate target.

Certain embodiments are to methods and/or systems or slowing a patient's breathing during sleep by using positive pressure therapy comprising the steps of setting an interim breathing rate target, increasing the magnitude of a variable pressure waveform that is scaled to the interim breathing rate target if the patient's breathing rate is greater than the interim breathing rate target in order to lengthen the patient's breath duration, the magnitude of the pressure increase being a function of the difference between the interim breathing rate target and the patient's breathing rate, and reducing the interim breathing rate target in response to the patient's breathing rate slowing down toward or below the interim breathing rate target.

Certain embodiments are to methods and/or systems for slowing a patient's breathing during sleep by using a ventilator coupled to a patient's airway comprising the steps of setting an interim breathing rate target, increasing the air supplied to the patient's airway from the ventilator during patient breaths if the patient's breathing rate is greater than the interim breathing rate target in order to lengthen the patient's breath duration, reducing the interim breathing rate target in response to the patient's breathing rate slowing down toward the interim breathing rate target, and interrupting the air increase and interim breathing rate target reduction steps if the patient exhibits opposition to breath duration lengthening, the air increase and interim breathing rate target reduction steps being controlled to take place over a period of minutes to hours in the absence of patient opposition.

Certain embodiments are to devices for slowing a patient's breathing during sleep by using positive pressure therapy comprising a blower for applying a variable pressure waveform to the patient's airway, at least one sensor for detecting the breathing rate of the patient, and a controller for setting a current interim breathing rate target, causing the blower to periodically increase the magnitude of the pressure waveform when the patient's breathing rate is greater than the interim breathing rate target in order to lengthen the patient's breath duration, and periodically reducing the interim breathing rate target in response to detection of the patient's breathing rate slowing down toward the current interim breathing rate target.

Certain embodiments are to devices for slowing a patient's breathing during sleep by using positive pressure therapy comprising a blower for applying a variable pressure waveform to the patient's airway, at least one sensor for detecting the breathing rate of the patient, and a controller for setting an interim breathing rate target, causing the blower to increase the magnitude of a variable pressure waveform that is scaled to the interim breathing rate target if the patient's breathing rate is greater than the interim breathing rate target in order to lengthen the patient's breath duration, the magnitude of the pressure increase being a function of the difference between the interim breathing rate target and the patient's breathing rate, and reducing the interim breathing rate target in response to the patient's breathing rate slowing down toward the interim breathing rate target.

Certain embodiments are to devices for slowing a patient's breathing during sleep comprising a blower coupled to a patient's airway, at least one sensor for monitoring the breathing of the patient, and a controller for setting an interim breathing rate target, causing the air supplied to the patient's airway from the blower during patient breaths to increase if the patient's breathing rate is greater than the interim breathing rate target in order to lengthen the patient's breath duration, reducing the interim breathing rate target in response to the patient's breathing rate slowing down toward the interim breathing rate target, and interrupting air increase and interim breathing rate target reduction if the patient exhibits opposition to breath duration lengthening, the controller causing the air increase and interim breathing rate target reduction to take place over a period of minutes to hours in the absence of patient opposition.

In certain embodiments, the variable pressure waveform cycles from an inhalation phase to an exhalation phase when the patient airflow decreases to a cycle threshold, the cycle threshold being a function of flow versus time within a breath and generally increasing with time.

In certain embodiments, the different interim breathing rate targets have different cycle threshold functions, and the cycle threshold functions allow easier cycling as the interim breathing rate targets decrease.

In certain embodiments, the variable pressure waveform triggers from an exhalation phase to an inhalation phase when the patient airflow increases to a trigger threshold, the trigger threshold being a function of flow versus time within a breath and generally decreasing with time.

In certain embodiments, the different interim breathing rate targets have different trigger threshold functions, and the trigger threshold functions allow easier triggering as the interim breathing rate targets decrease.

In certain embodiments, the magnitude of the pressure waveform is decreased if the patient's breathing rate is less than the interim breathing rate target.

In certain embodiments, the magnitude of a pressure increase or decrease is a function of the difference between the interim breathing rate target and the patient's breathing rate.

In certain embodiments, the interim breathing rate target is reduced along a predetermined path, but the reduction is paused if the patient's breathing rate is excessively high for the current interim breathing rate target.

In certain embodiments, the duration of the pressure waveform is adjusted in accordance with the current interim breathing rate target.

BRIEF DESCRIPTION OF THE DRAWINGS

Certain illustrative embodiments will now be described, by way of example only, with reference to the accompanying drawings, in which.

DETAILED DESCRIPTION

Figure 1:
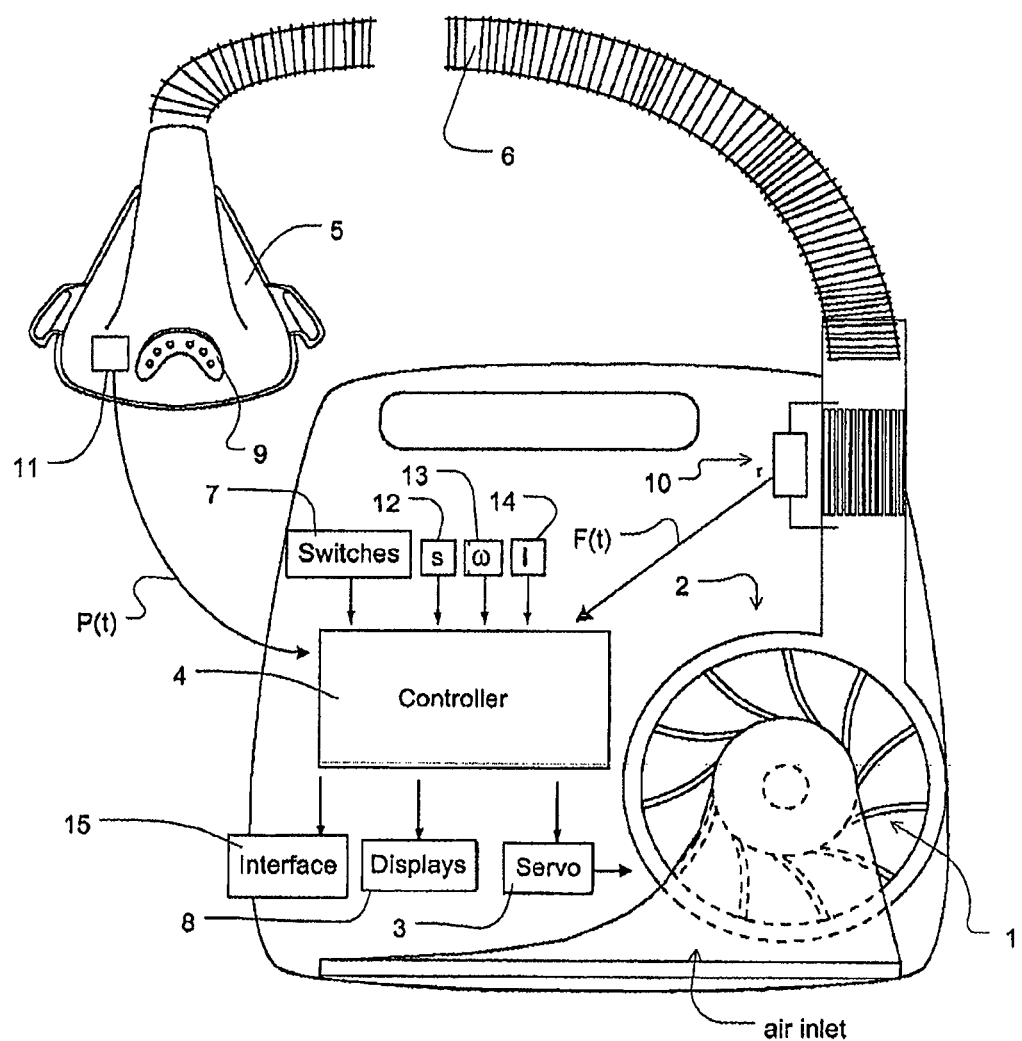
FIG. 1 shows apparatus according to certain embodiments.

FIG. 1 shows, by way of example, apparatus suitable for performing certain disclosed embodiments. The apparatus includes an impeller 1 connected to an electric motor 2 under the control of a servo-controller 3 which is in turn under the control of a controller 4. In one form the controller 4 is a micro-processor based controller. The impeller 1 and motor 2 form a blower. Air from the blower passes along a flexible conduit 6 to a patient interface such as a nasal mask 5 with a vent 9. While a nasal mask is illustrated, certain disclosed embodiments may be used in conjunction with a nose-and-mouth mask, full face mask, endotracheal tube or other devices that perform the desired function. A number of switches 7 are connected to the controller. A number of sensors are also connected to the controller, namely, sensors for flow 10, pressure 11, snore 12, motor speed 13 and motor current 14. A set of displays 8 connected to the controller 4 display information from the controller.

An interface 15 enables the controller 4 to communicate with an external device such as a computer. With such a device, changes in the speed of the blower may be controlled to alternatively change the pressure in the mask to implement ventilatory support. Optionally, the blower motor speed may be held generally constant and pressure changes in the mask may be implemented by controlling an opening of a servo-valve (not shown) that may variably divert/vent or deliver airflow to the mask. Those skilled in the art will recognize other devices for generating ventilatory support and delivering same to a patient.

The controller 4 or processor is configured and adapted to implement certain of the methodologies described herein and may include integrated chips, a memory and/or other instruction or data storage media. For example, programmed instructions with the control methodology may be coded on integrated chips in the memory of the device or such instructions may be loaded as software. With such a controller, the apparatus can be used for many different pressure ventilation therapies simply by adjusting the pressure delivery equation that is used to set the speed of the blower or to manipulate the venting with the release valve. Those skilled in the art will also recognize that aspects of the controller may also be implemented by analog devices or other electrical circuits.

The apparatus can further include a communication module, for example, a wireless communication transceiver and/or a network card, for communication with other devices or computers such as hand-held display and control devices. The apparatus optionally includes an oximeter in the main blower housing. A sense tube may be connected to the main housing of the blower or the mask to allow the apparatus to sense oxygen concentration and pressure levels in the mask. The apparatus may further include additional diagnosis units such as a pulse oximeter and respiratory movement sensors. The unit may also include a set of electrodes for detecting cardiac rhythm.

It is understood that a combination of devices and/or computers linked by available communications methods may be used to accomplish the desired goals. For example, the apparatus can interface with a variety of hand-held devices such as a Palm Pilot via wireless communication. With such a device, a physician may, for example, remotely monitor, analyze or record the status or data history of a patient or diagnose the severity of the patient's condition using the device. Furthermore, the treatment program that is being run on the patient can be monitored and changed remotely.

Figure 2A:
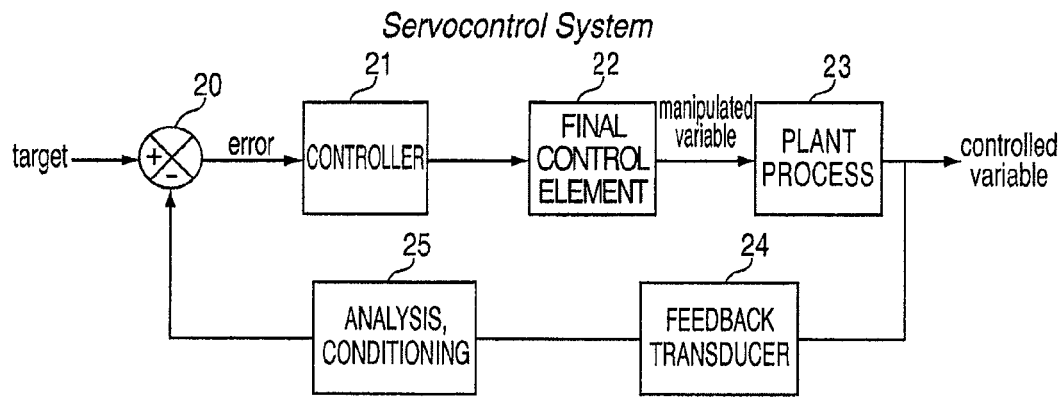
FIG. 2A is a generalized block representation of a closed-loop (feedback) control system, in accordance with certain embodiments.

The generalized closed-loop servo control system of FIG. 2A operates with a 'target' input, which is the desired value for some output parameter of the servo system. A 'controlled variable' determines the output parameter and is often the output parameter itself. A feedback transducer 24 measures the controlled variable and an analysis and conditioning system 25 derives a signal that represents the controlled variable in the same terms as the target input. Subtractor 20 generates an error signal which controller 21 and perhaps one or more additional control elements such as final control element 22 shown in the drawing operate on to derive a manipulated variable. That variable affects a plant process 23 to generate the controlled variable that is fed back.

Figure 2B:
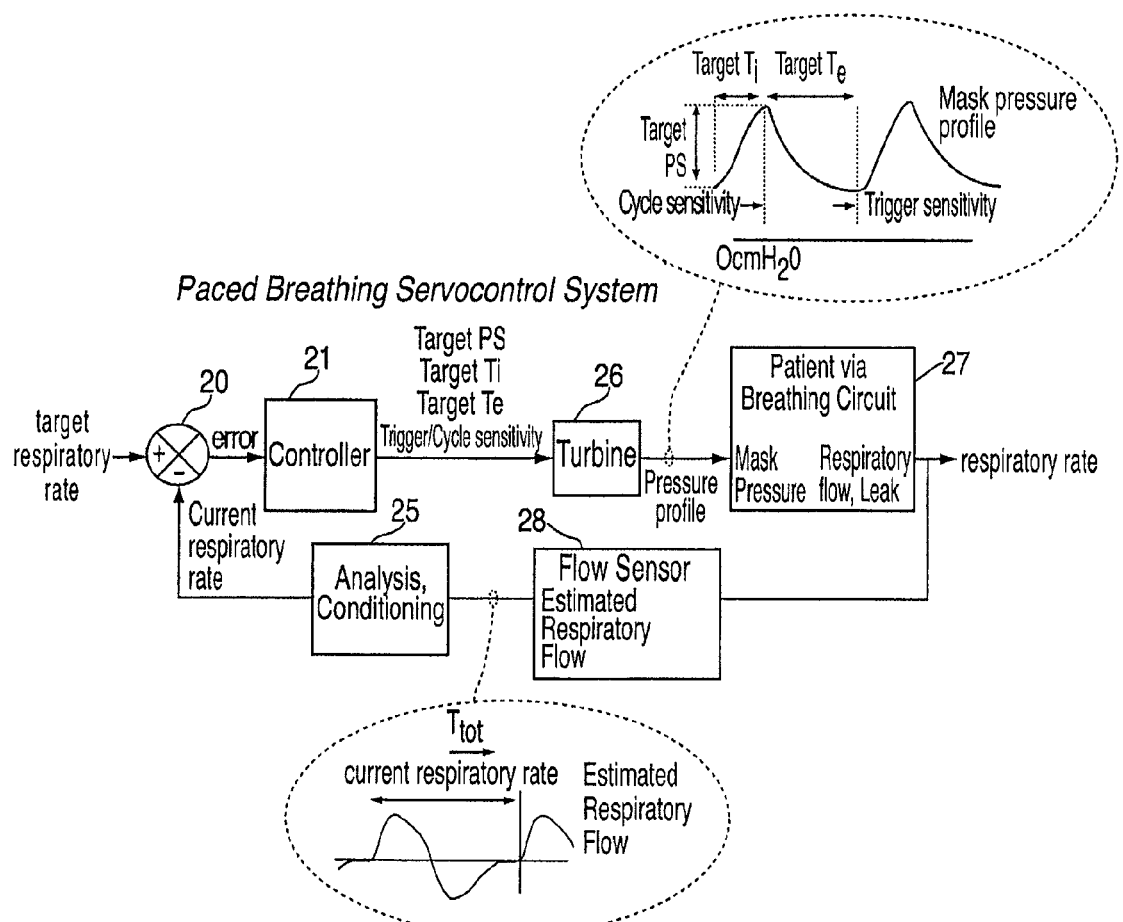
FIG. 2B, which is based on FIG. 2A, depicts a closed-loop controller for paced breathing, with the ultimate aim of maintaining a low respiratory rate optimized for a condition of interest, within limits achievable for a given patient, in accordance with certain embodiments.

FIG. 2B illustrates how the servo system of certain embodiments satisfies the generalized closed-loop system of FIG. 2A. The controlled variable is the patient's respiratory rate, and the target input is the desired (interim) respiratory rate. The error signal, which represents the difference between the actual and desired respiratory rates, is fed to the controller which derives a number of variables that are used in the processing. Two of these are Target Ti and Target Te. Target Ti is an interim desired time interval for the inspiratory phase of a breath. It is not the final desired inspiratory time interval. It is only the desired interval at the present time, on the way toward a longer inspiratory interval at the end of the overall process. The same applies to Te, the interim desired expiratory time interval.

As the total breath interval lengthens (as Ti and Te lengthen individually), the pressure support increases since more air must be supplied during each breath to compensate for fewer breaths overall. Thus there is a Target PS that is derived as well, an interim value that represents the magnitude of the pressure waveform. The minimum pressure is fixed, so PS determines the maximum pressure.

The fourth and fifth variables derived by the controller based on the present error are Trigger sensitivity and Cycle sensitivity. The former represents the value of patient air flow during expiration that will cause the machine to switch from an expiratory phase to an inspiratory phase, and the latter represents the value of patient air flow during inspiration that will cause the machine to switch from an inspiratory phase to an expiratory phase. The five variables control the turbine or other mechanism used to supply pressure to a patient mask or other patient interface, which may be any commercial blower and mask used by CPAP patients, and the five variables are shown in the waveform that represents the pressure profile at the output of the turbine. The pressure applied rises to the Target PS level near the end of the interim Target Ti. When the air flow is such that the Cycle sensitivity threshold is reached, the machine switches to its expiratory phase. The pressure then decreases toward the minimum level near the end of the Target Te interval. When the air flow is such that the Trigger sensitivity threshold is reached, the machine switches to its inspiratory phase.

Referring back to the generalized block diagram of FIG. 2A, the plant process is the patient himself/herself. The input to the process is the pressure in the mask (indicated as the pressure profile). There are many parameters that are affected in the control process, including, but not limited to, respiratory flow and leak flow, but the output of interest is respiratory rate. The feedback transducer of FIG. 2A is in this case flow sensor 28. The sensor estimates the respiratory flow, and from this the analysis and conditioning circuit 25 determines the current (interim) respiratory rate. This is the rate that is used to derive the error. The individual functions of the servo system of FIG. 2B are performed by standard commercial CPAP machines.

The waveform shown at the output of flow sensor 28 is the estimated respiratory flow. It is the current rate that is of interest and used in the error calculation. The waveform also shows the value of Ttot, the total time duration of the current breath (the reciprocal of the current respiratory rate). The sum of Target Ti and Target Te, shown in the waveform at the output of turbine 26, equals Ttot.

In certain embodiments, the pressure waveform is not two-valued as it is in other bi-level systems. A template is used for the pressure profile, as disclosed in many prior art patents. The turbine is controlled to provide a pressure waveform that follows the template. The amplitude may vary with PS, and the time may vary as the two target values change, but the shape remains the same. It is as though the two axes of the waveform are shortened and lengthened, as the shape remains constant. However, it is not necessary that the shape remain constant, and even a square-shaped or trapezoidal bi-level waveform can be used although it is generally recognized that in non-obstructed lungs, rapid pressurization such as with a square waveform tends to increase rate rather than decrease it. Similarly, it is not necessary to have a fixed lower pressure (determined by the physician) and a variable upper pressure, as standard titrating mechanisms can be employed as well.

Figure 3A:
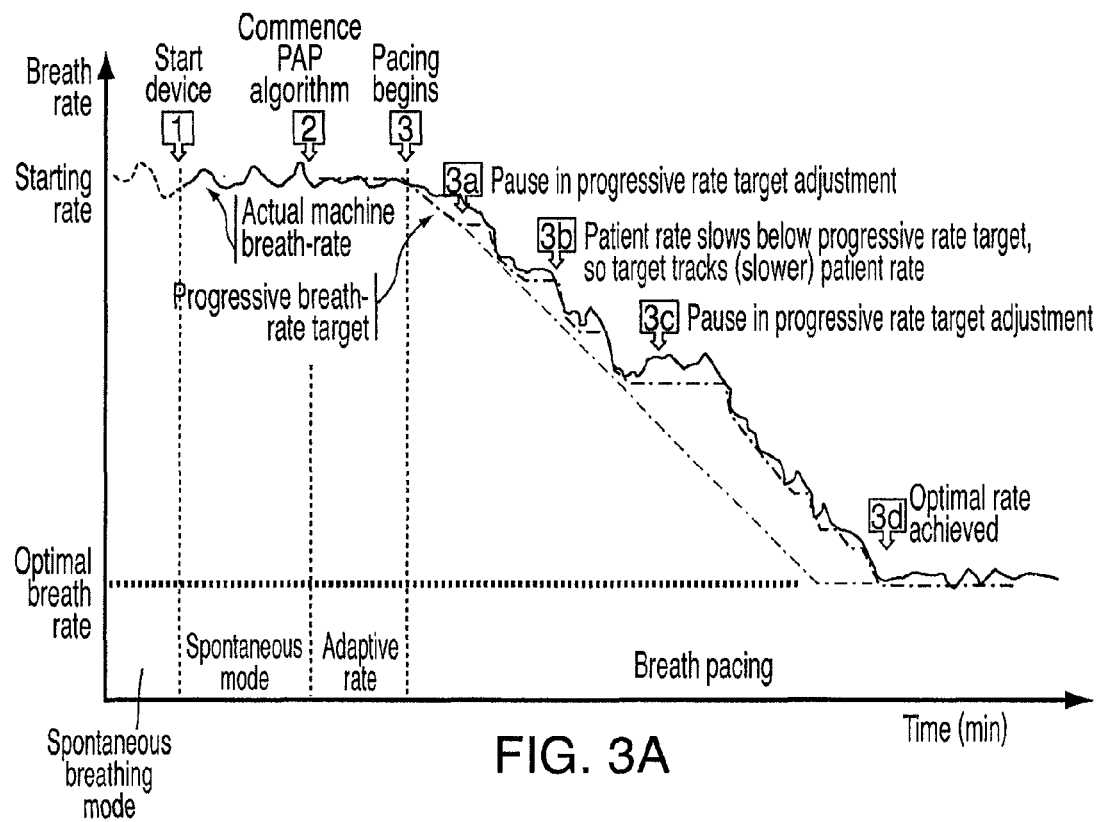
FIGS. 3A and 3B are general (within-session) time-courses for breath pacing therapy towards the optimal breath rate, showing respectively breath rate and pressure support, in accordance with certain embodiments.
Figure 3B:
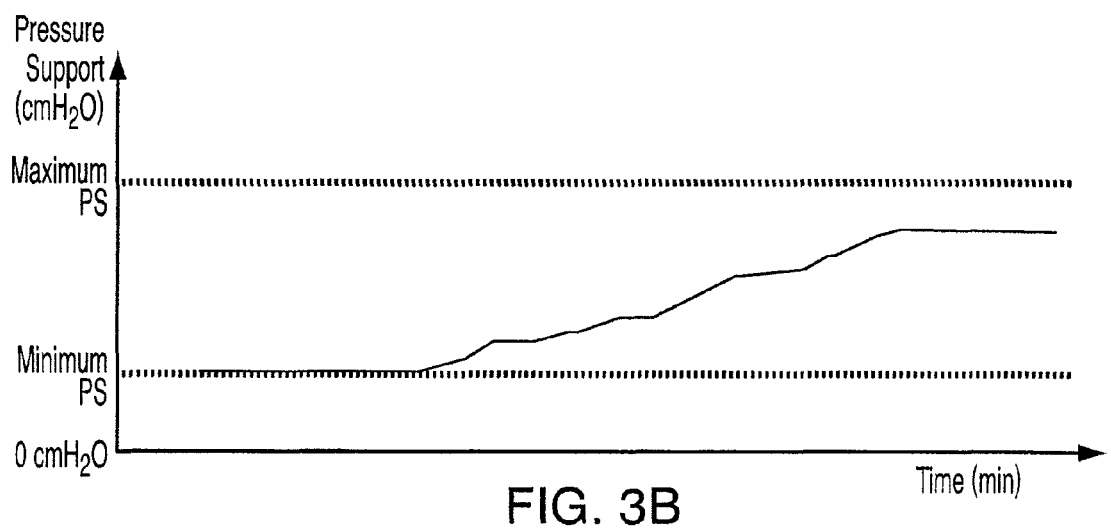

FIGS. 3A and 3B are general (within-session) time-courses for breath pacing therapy towards the optimal breath rate, showing respectively breath rate and pressure support. The initial portion depicts spontaneous breathing. When the device is first applied to the patient (event 1), a comfortable variable-level therapy regime is commenced (using the standard pressure profile template), with the machine rate dictated by the patient's spontaneous breathing (spontaneous mode). The operation is similar to standard VPAP therapy, with changes in machine phase following the patient's breathing. At the commencement of the positive airway pressure (PAP) pacing algorithm (event 2), the therapy adopts an initial target breath rate adapted to the patient's own rate (solid dashed trace). After a prescribed settling time, the algorithm encourages a progressively slower rate, i.e., breath pacing (event 3). Through incremental adjustment of pressure support, and trigger/cycle thresholds, the target rate is incrementally slowed, the long-term goal being to achieve an optimal breath-rate (event 3d), as set by the clinician. How variables are adjusted will be described herein. The progressive breath-rate target contour (faint dashed line) that is followed to achieve this optimal rate may be any shape (linear descent is shown), and is revised (events 3a, 3b, 3c) along the way according to the patient's progress towards the target. The target rate is only an "interim" target rate—the servo control adjusts the pressure so as to slow down the breath rate so it meets the interim target, following which a new, lower interim target comes into play. The result is a standard-type of servo control, with the input changing to conform to a predetermined strategy but at a speed that depends on the patient's progress.

It will be seen from FIG. 3A that when the patient breath rate (solid line) does not conform to the reducing target rate, i.e., when the patient breath rate is too high, the target rate remains fixed until the patient rate "catches up" (by slowing down). Only then does the interim target rate continue on its downhill traverse. The delay causes a new progressive breath-rate target contour to be followed but, in the illustrative embodiment, with more or less the same slope.

Event 3*a* in FIG. 3A is the first occurrence of the patient's breath rate not slowing down sufficiently to track the interim target. The continuously decreasing interim rate target stops changing and remains constant. The pressure is now increased, as reflected in FIG. 3B. As the pressure is increased, the patient's breath rate decreases until it matches the interim target, at which time the target resumes its downward slide. (Actually, as will become apparent from the flow chart of FIG. 10, a "match" occurs when the patient rate may still be a tiny bit higher than the interim target rate. Being close enough is sufficient reason to lower the interim target rate another increment.) Similar remarks apply to events 3*b* and 3*c*. Event 3*b* also shows what happens when the patient breath rate actually dips below the interim target, which will be discussed herein. In most cases, the target decreases until it is below the patient rate so that the breath pacing (increased pressure) can still further lower the patient rate.

The settling period referred to herein occurs (at least the first time) during sleep onset, where breathing is largely spontaneously triggered. The goal here is to offer comfortable, calming and/or minimal breathing assistance. The duration of the settling period can vary, for example, shorter for diurnal treatment sessions and longer for going to sleep.

During the adaptive rate phase the machine adapts to the patient's own average rate. The difference between this and operation in the spontaneous mode may be small, and sometimes less important. The difference is that while in the spontaneous mode the machine follows the patient's efforts in most instances regardless of the rate, in the adaptive rate mode there is a target rate which the trigger/cycle thresholds to be described herein aim to encourage. The PAP algorithm starts from the base rate determined during the adaptive mode, and it is to this base rate that the machine reverts when the patient arouses, as will be described.

FIG. 3B depicts how the pressure support (PS) variable increases as the breath rate decreases. Exactly how the pressure changes is part of the algorithm for decreasing the breath rate, and will be described below. The general idea is to increase the pressure slightly in order to lengthen the breath duration—since the increased pressure delivers greater volume to the patient, the patient spontaneously slows down the breathing. Those parts of the pressure curve that are flat reflect minimal feedback 'error'—the breath rate is close enough to the interim target rate that there is often no need to increase the pressure.

Figure 4:
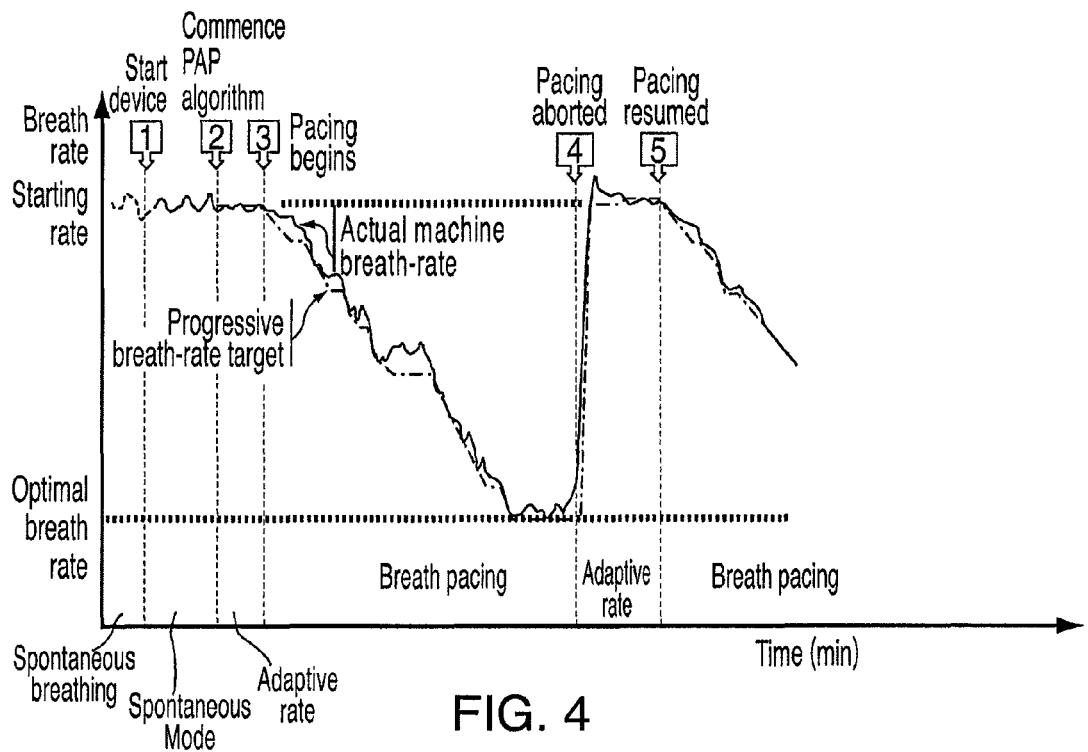
FIG. 4 is similarly a (within-session) time-course for breath pacing therapy, responding to patient opposition, in accordance with certain embodiments.

FIG. 4 depicts a within-session time-course for breath pacing therapy, in which the optimal breath rate was achieved, but the patient's breathing rate then increased well above the optimal rate. In response to the patient clearly preferring a significantly higher rate (event 4), pacing is aborted and the initial adaptive rate is restored, following which the overall algorithm is executed once again. After stable breathing is resumed and the settling time is satisfied, pacing is re-commenced (event 5). Basically, FIG. 4 reflects a recognition that breath pacing may fail, in which case the whole process starts over again, using the previously determined adaptive rate. (It is, of course, possible to start over at the very beginning with event 1, although in most instances it is not believed to be necessary.)

Figure 5:
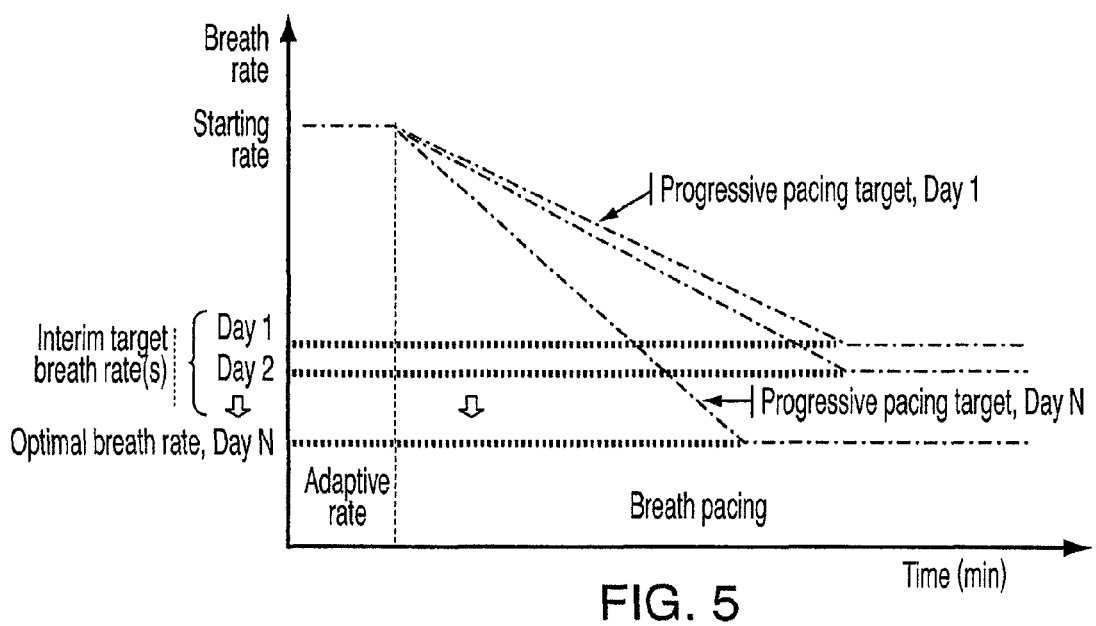
FIG. 5 is a conditioning time-course for breath pacing therapy, showing how the optimal breath rate may be achieved over many days, in accordance with certain embodiments.

A conditioning time-course for the breath pacing therapy, showing how the optimal breath rate may be achieved over many days/nights/weeks, is depicted in FIG. 5. Optimal rate targets may be different for successive days, and they get lower and lower. On each day, for the given slope, pacing takes place along a different path toward a different optimal target. Also illustrated is a change in the pacing algorithm's nominal assertiveness, where the deceleration in breath-rate is greater as the patient becomes conditioned to slow breathing (i.e., the gradient of the progressive pacing target gets steeper from day to day). If not fixed in the machine, the progressive breath-rate target contour for each session can be set by the patient or physician. Alternatively, the machine can keep track of the overall course of therapy and adjust the target contours automatically (not shown in the flow chart of FIG. 10).

Figure 6A:
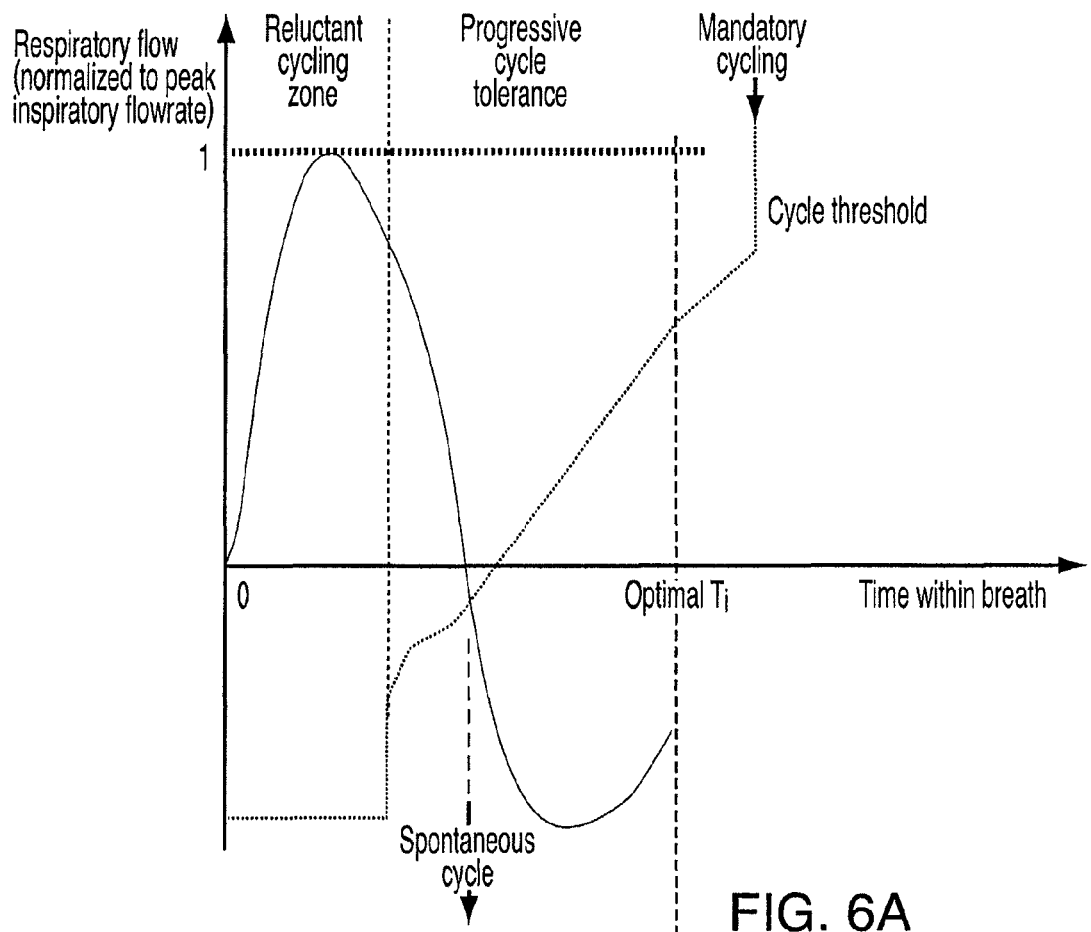
FIGS. 6A and 6B depict cycling behaviour, aiming to progressively extend the inspiratory phase, early in the rate-lowering process where the interim target inspiratory time (progressive Ti target) is considerable shorter than the optimal Ti, in accordance with certain embodiments.
Figure 6B:
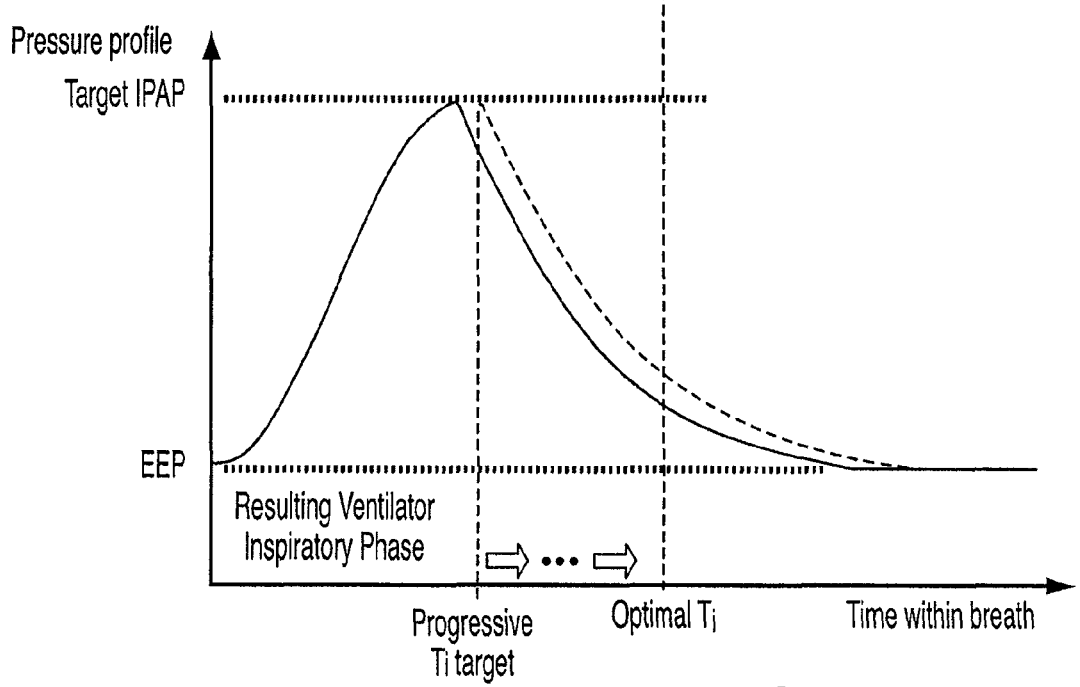

One of the primary mechanism that promotes slower breathing is a larger tidal volume (air breathed per breath) delivered via controlled, progressive pressurization during inspiration, and controlled de-pressurization during expiration. This process is assisted by reluctant triggering and cycling that discourage a faster rate; easier triggering and cycling of each breath phase is allowed only as the patient approaches the interim target rate. FIGS. 6A and 6B illustrate the time course of flow and pressure for an individual breath during inspiration early in the rate-lowering process.

The drawing shows the optimal Ti, the time from the start of inspiration at the left end of FIG. 6A to the end of inhalation when ideally the expiratory phase of the cycle should begin. The patient has not yet progressed to this level, however, and for the cycle depicted there is a progressive or interim target Ti (see FIG. 6B) that is shorter than the optimal Ti. For every target Ti there is a cycle threshold function or plot. The plot of FIG. 6A is for the particular interim Ti shown in the drawing. It will be seen later in FIG. 7A that the cycle threshold plot for a different Ti value is different.

Toward the end of inhalation, the flow will have decreased to the point that it crosses the cycle threshold at some time during the inspiratory phase, at which point exhalation will begin. In the example shown, the cycle threshold is hit shortly before the target Ti is reached. The machine switches to its exhalation mode when the flow is slightly negative, as shown, i.e., very shortly after patient exhalation has begun. The pressure, at the usual end-expiratory level (EEP) at the start of inspiration, did not quite rise to the target IPAP level, the maximum inspiratory pressure (minimum pressure plus current PS value). Since a spontaneous cycle has taken place with the patient starting to exhale slightly before the end of the desired Ti interval, the pressure now follows the expiratory phase of the pressure profile. (see FIG. 6B) (The dashed lines in FIG. 6B show what the pressure waveform would have been had the progressive Ti target been reached.)

The significance of the cycle threshold curve should be appreciated. At the start of the inhalation phase, there is a 'reluctant' cycling zone. The patient would need to oppose the inspiratory pressure for the threshold to be reached and it is inhalation (positive flow) that is just starting. But after some virtually guaranteed inspiratory machine operation, it becomes easier and easier to cycle the machine to its exhalation mode. Cycling occurs as the flow decreases, but the threshold is crossed with higher flow later and later in a cycle. Thus the sensitivity increases, and it becomes easier to cycle (i.e., while the positive flow is still significant) as the inspiratory phase lengthens.

When the inspiratory phase is relatively long, cycling is caused to take place while the patient is still inhaling, which is evident from FIG. 6A which shows the cycle threshold being positive as the length of the inhalation phase approaches the Optimal Ti. Traditionally, ventilators do cycle (switch to exhalation mode) while flow is still inspiratory. That is because breathing against inspiratory pressure is uncomfortable and takes exertion. The cycle criterion is traditionally between 75% and 25% of peak inspiratory flow. However, because the goal here is to prolong Ti beyond what is natural, the cycle threshold curve advantageously requires a greater drop in inspiratory flow than is usual before cycling takes place.

It should be noted that if the flow does not cross the cycle threshold curve by some predetermined time interval after the Optimal Ti, mandatory cycling takes place. The machine switches to exhalation operation.

Figure 7A:
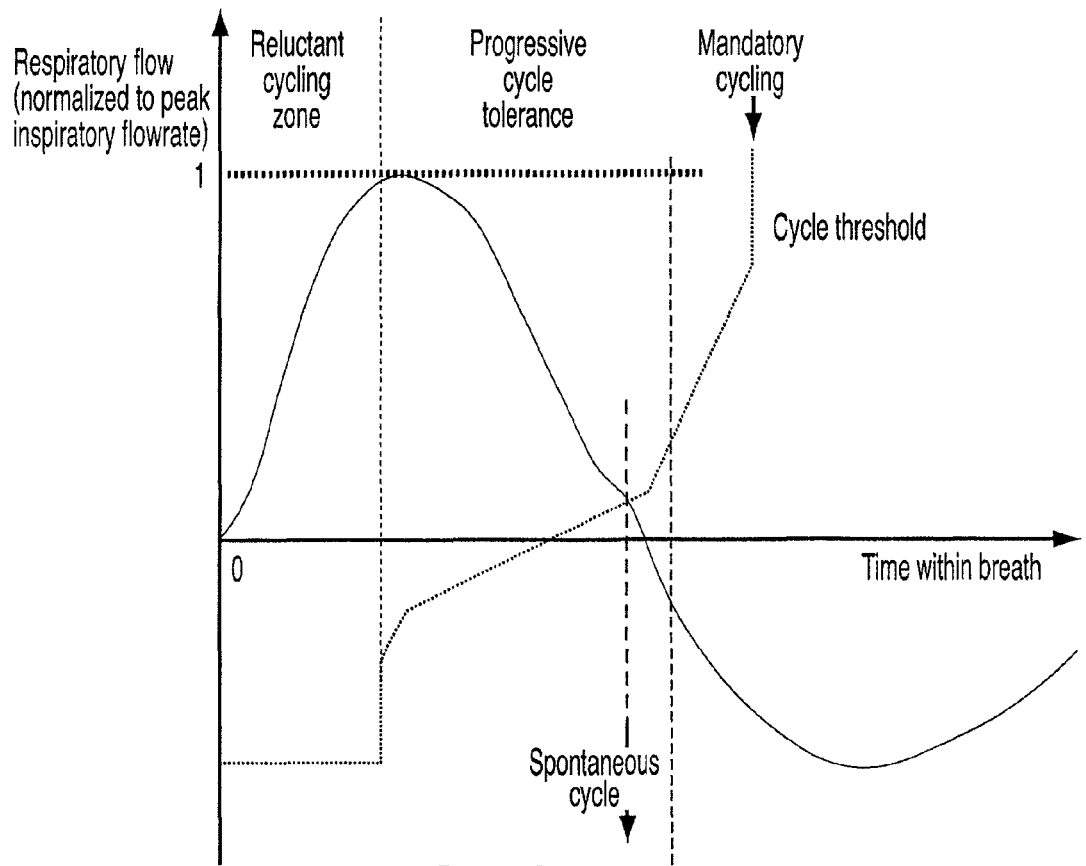
FIGS. 7A and 7B depict cycling behaviour, aiming to progressively extend the inspiratory phase, towards the end of the rate-lowering process, where the patient's spontaneous inspiratory phase is almost at the optimal Ti, in accordance with certain embodiments.
Figure 7B:
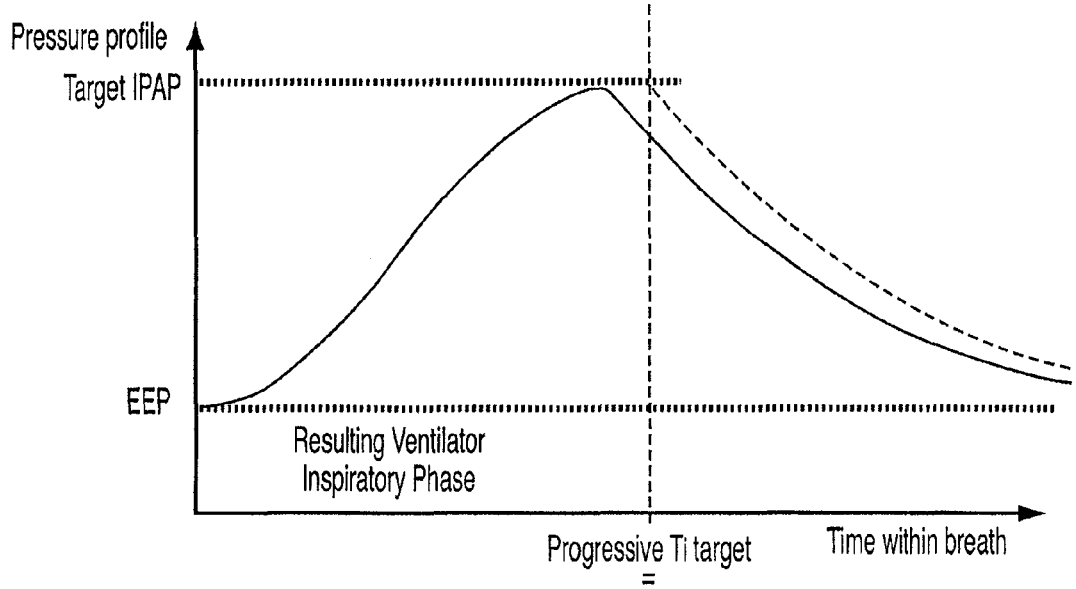

FIGS. 7A and 7B are similar to FIGS. 6A and 6B, but here it is assumed that the progressive Ti target has progressed all the way to the optimal Ti. Now, because inhalation takes longer, the flow does not intersect the cycle threshold curve until almost at the end of the desired Ti interval. A spontaneous cycle occurs and the expiratory phase of the pressure template controls the applied pressure.

The important difference between FIGS. 6A and 7A is that the cycle threshold curves are different. The cycle threshold curve that applies during any cycle depends on the interim rate target. (For each value of the target, there is a respective cycle threshold curve.) To encourage the patient to become accustomed to a longer inspiratory phase, cycling to the expiratory phase is made easier as the breath lengthens. Note that the flow does not have to decrease as much in FIG. 7A as it does in FIG. 6A in order for the machine to cycle to its exhalation phase.

Figure 8A:
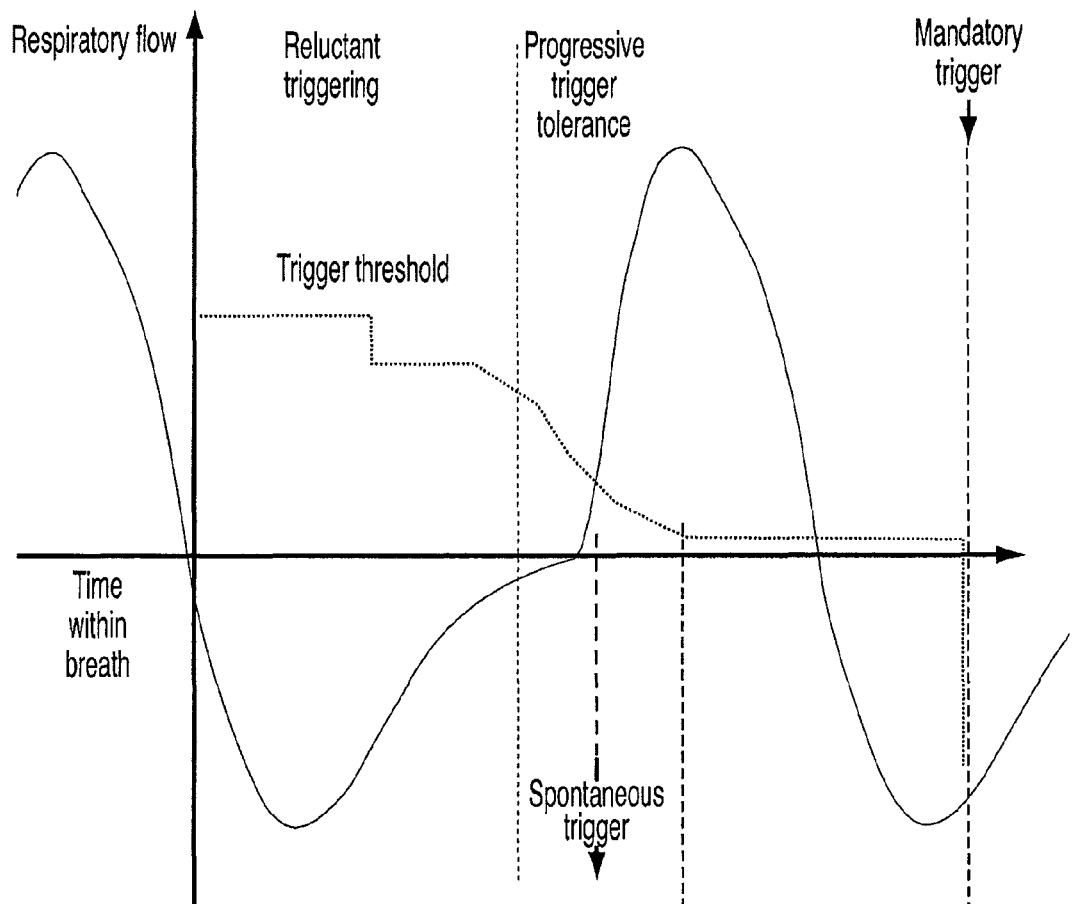
FIGS. 8A and 8B depict triggering behaviour, aiming to progressively extend the expiratory phase, early in the rate-lowering process where the interim target expiratory time is considerably shorter than the optimal target Te, in accordance with certain embodiments.
Figure 8B:
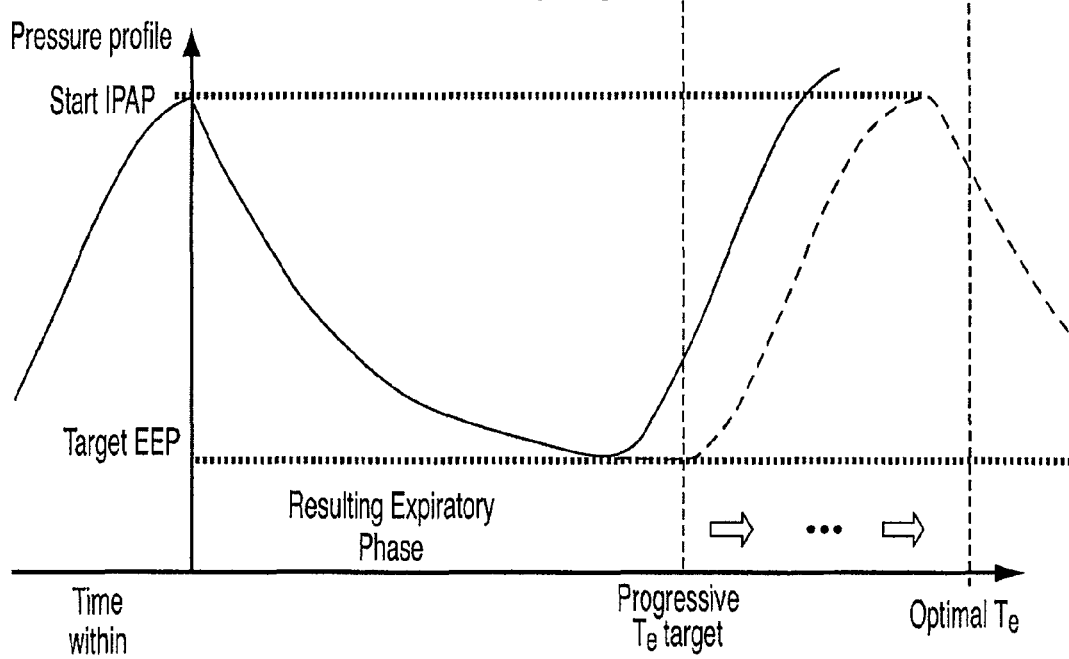

FIGS. 8A and 8B are similar to FIGS. 6A and 6B, but they show the expiratory phase of a cycle, where triggering—the start of machine inspiratory operation—occurs early in the rate-lowering process when the progressive Te target is well below the optimal Te. (The several figures are not drawn to scale.) The pressure lowers from the starting IPAP value to the target EEP. The trigger threshold curve is very positive in the early part of the expiratory phase, giving rise to a 'reluctant' triggering region in which requires forceful inspiratory effort by the patient for triggering to take place. As time progresses during the expiratory phase, it becomes easier and easier to trigger as less positive flow is required to cause the machine to switch to its inhalation mode of operation. (While a switch to exhalation mode takes place while the patient is still inhaling, as discussed herein, a switch to inhalation mode occurs only after the patient has started to inhale, as is usual with conventional ventilators.)

Figure 9A:
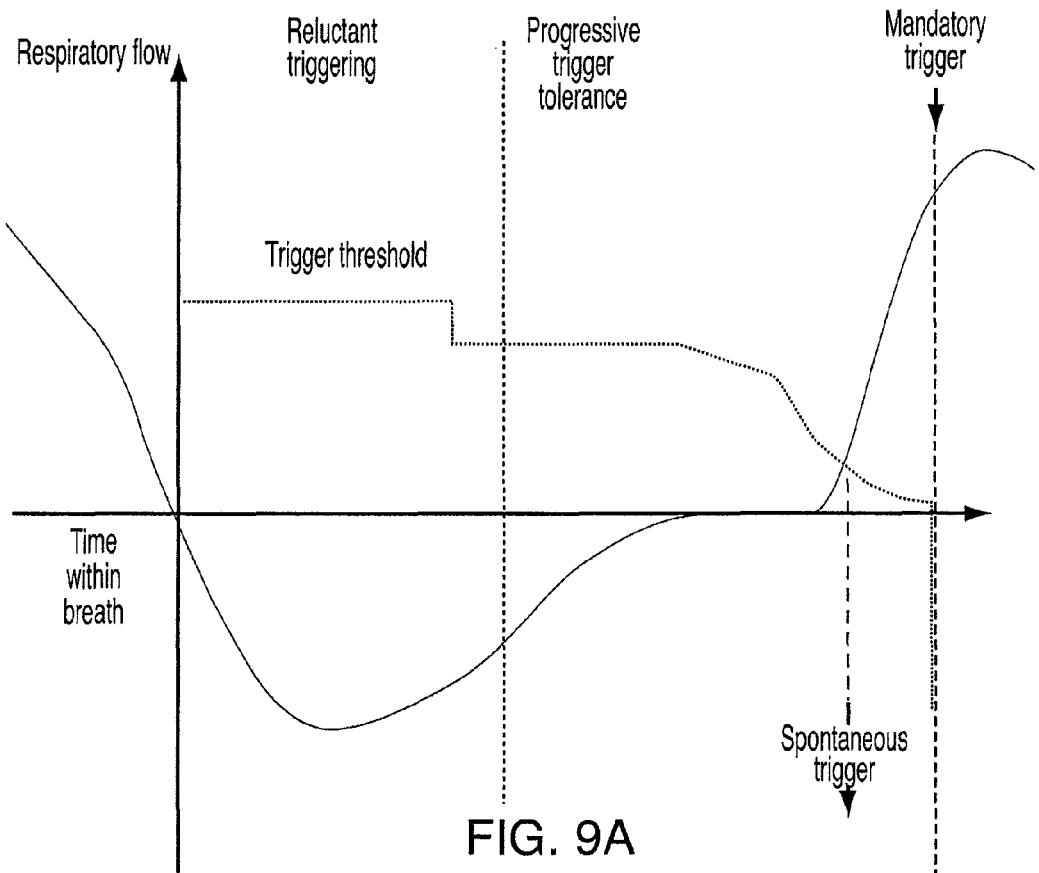
FIGS. 9A and 9B depict triggering behaviour, aiming to progressively extend the expiratory phase, towards the end of the rate-lowering process, where the patient's spontaneous expiratory phase is almost at the optimal Te, in accordance with certain embodiments.
Figure 9B:
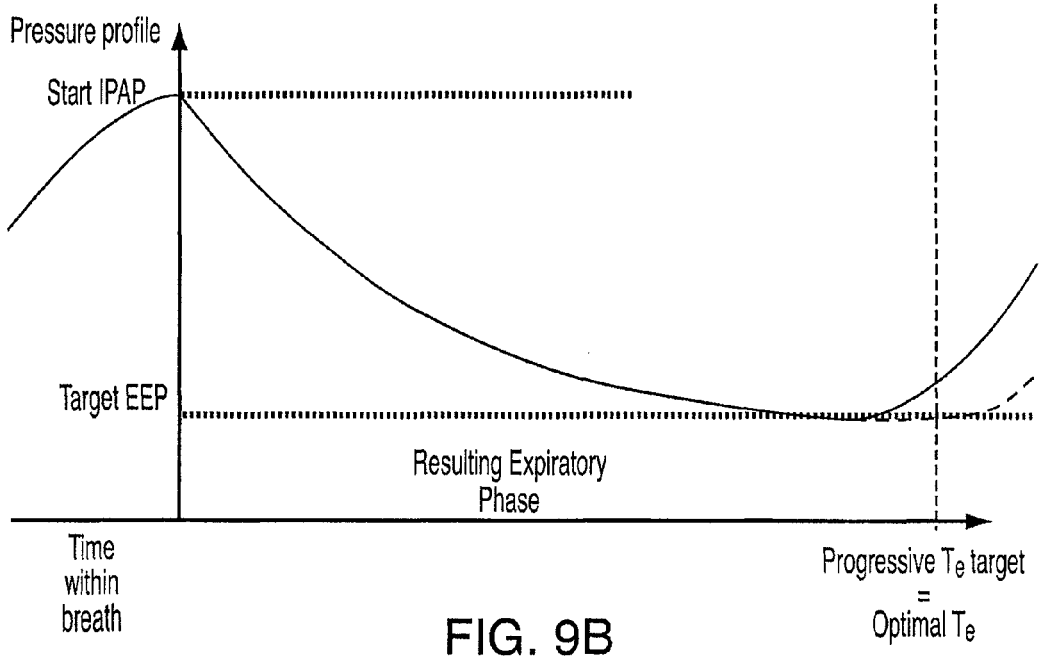

FIGS. 9A and 9B show what happens toward the end of the rate-lowering process, where the patient's spontaneous expiratory phase is almost at the optimal Te and the interim target Te is already there. Shown is a spontaneous trigger just short of the target Te. Comparing FIGS. 8A and 9A, it should be noted that the flow does not have to increase as much in FIG. 9A as it does in FIG. 8A in order for the machine to trigger to its inhalation phase. Should the optimal Te be achieved without spontaneous triggering, a machine trigger may be invoked. In general, the algorithm assumes a target Ti and a target Te at the start of a breath, but the target profiles may be truncated at a point if the patient satisfies the trigger/cycle criteria.

Figure 10:
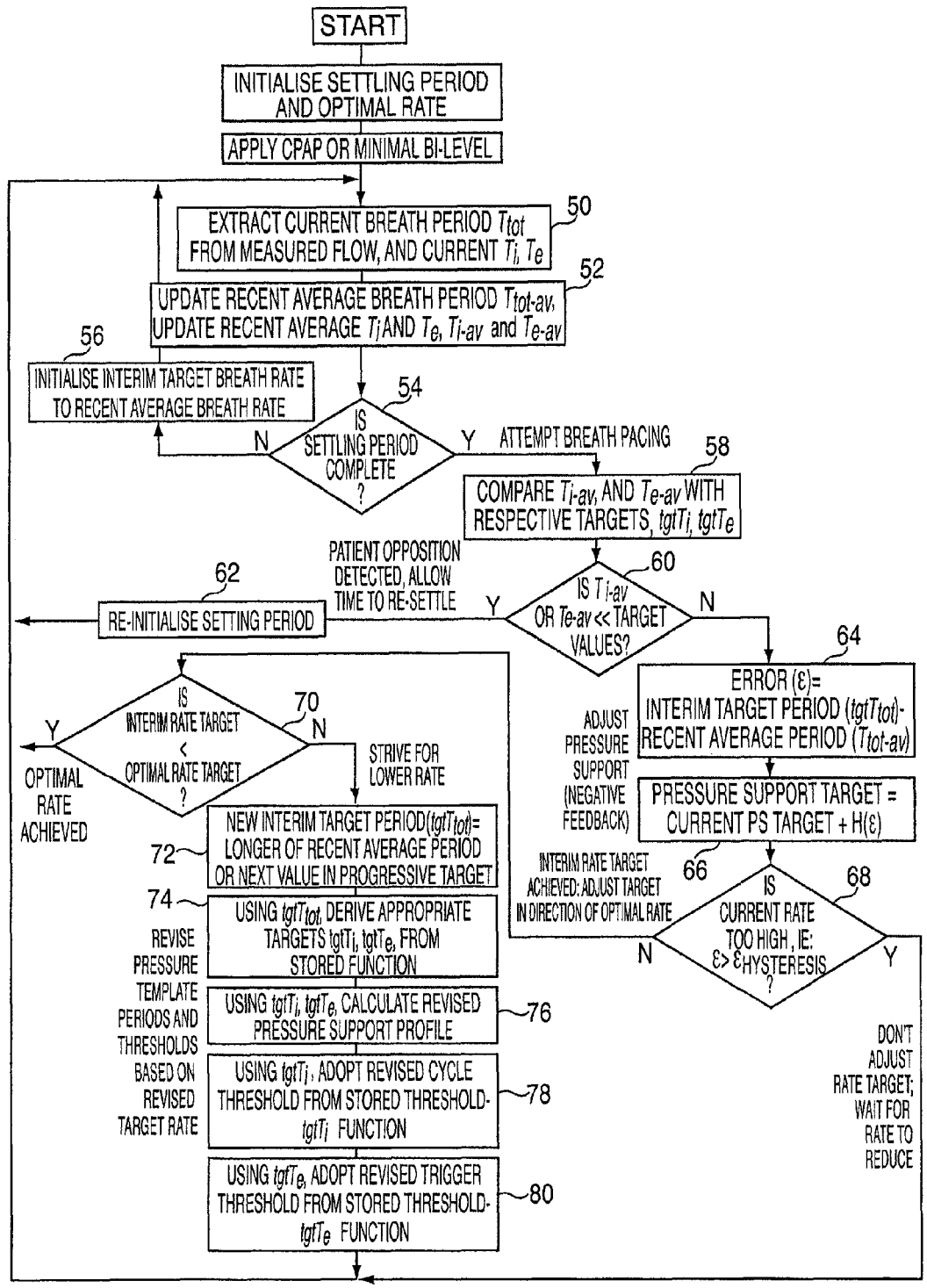
FIG. 10 shows the flow control logic for the breath-pacing algorithm, in accordance with certain embodiments.

Referring to the flow chart of FIG. 10, at the start of the machine process, the optimal Ti and Te are determined (typically, set by the physician), the settling period (about 20 minutes) is initialized, and PAP (bi-level, but preferably following a template as shown in the drawings) is applied. The actual current Ti and Te values are determined, as shown in step 50, along with the actual current breath period Ttot that is the reciprocal of the current respiratory rate derived by the analysis and conditioning block shown on FIG. 2B.

In step 52, three average values are calculated—the recent average breath period, Ttot-av, and the recent average inspiratory and expiratory intervals, Ti-av and Te-av. The averages are calculated over an interval ranging from a few breaths upward. The three values are moving averages, as is known in the art, the oldest sample values being replaced by the most recent sample values in the average calculations. These average values are the ones used in comparing the current breathing rate and its Ti and Te components to any instantaneous value of interim target rate and its associated Ti and Te intervals.

Referring to FIG. 3A, it will be recalled that there is an interim breath rate target that progressively decreases, but at any instant it is the current value of the interim target that is the input to the servo control. The current target is based on the time that has expired since the start of the progression as well as the progress of the patient's breathing, as discussed herein in connection with FIG. 3A. The current breath rate target is also a function of the particular breath rate 'curve' (exemplified as straight lines in FIG. 3A) that is being followed, a new desired progression being put in place whenever the actual breath rate is too high and the progressive rate needs adjustment (events 3a, 3b and 3c in FIG. 3A). The breath rate 'curve' may also be a function of the particular day in the processing, as discussed herein in connection with FIG. 5. The physician can input the day from which the controller can determine the starting slope, or the controller can simply keep track of the treatment day and automatically determine the starting slope.

At any given time the controller knows not only the interim breath rate target, but also both Ti and Te target components of it. The components are easily determined by providing a table or even a formula (e.g., a fixed ratio) of Ti/Te pairs for each target breath rate. The algorithm compares the actual current average Ti with the interim target Ti (tgtTi) and it compares the actual current average Te with the interim target Te (tgtTe). The average and interim target time intervals are the same at the start of the processing, and the underlying pacing mechanism increases the pressure gradually so that the time intervals can be increased (i.e., the rate is lowered).

In certain embodiments, it is during the settling period that the target values are set equal to the actual values. After the settling period, the actual breath pacing starts. In step 54, a test is performed to determine if the settling period is over. If not, in step 56 the interim target breath rate is initialized again to equal the current average breath rate. This means is that the current average breath rate is measured and the interim target breath rate is set equal to it. And for an interim target breath rate, the two target values Ti and Te are set, as described herein.

Once the settling period is over, breath pacing begins. During each iteration (iterations occur at intervals of from about 0.25 to 5 minutes), the test of step 54 is answered in the affirmative. In step 58, the two current average values of interest, Ti-av and Te-av, are compared with respective targets tgtTi and tgtTe that are associated with the current target rate. Initially, during the first attempt at breath pacing after the settling period, the average and target values will be the same since the targets are set to equal the averages in step 56. (However, even though at the start of the pacing Ttot-av equals tgtTtot, the individual respective inspiratory and expiratory components may differ.) But during subsequent passes the values will differ. If one or both of the current Ti and Te averages differs appreciably from the respective interim target value tgtTi and tgtTe, then the situation is that shown in FIG. 4—the patient is just not following the pacing and the whole process has to start all over again.

The actual test is in step 60—is either current average interval much too short compared with its respective target value? By too short is meant that pacing is just not working and the current iterations should be aborted. If either of Ti-av or Te-av is less than its respective target by a predetermined threshold value, indicating patient opposition to the current interim breathing rate, the whole process begins all over again in step 62 with a new settling period. The previously determined adaptive rate (see FIG. 3A) is used as the new interim target, and the process starts over again.

On the other hand, if the answer to the test of step 60 is in the negative, it means that while the current inspiratory interval may be greater than the target Ti or the current expiratory interval may be greater than the target Te, the difference is small enough that the servo control may correct it. What we have is an event such as 3a, 3b or 3c in FIG. 3A.

The 'error' in servo control terms is simply the difference between what is desired (at the moment, this is the current interim target period tgtTtot) and what is on hand (the current recent average breath period Ttot-av). The error is computed in step 64. In step 66 the pressure is changed—the current PS target (the maximum template value) is increased in accordance with a function H(E) that is dependent on the error. The H(E) function can be implemented by a PID (proportional-integral-derivative) controller, although it could also simply provide a slight linear increase in the pressure in an attempt to extend the breath interval and reduce the error. The magnitude of a pressure increment depends on how fast the iterations through the main processing loop occur. The more iterations there are per minute, the greater the pressure rise if in each iteration another increment is applied. Typically, the increment magnitude and the rate of iterations might be such that the pressure rises at a rate of 1-3 cmH2O per minute.

It is possible that the error will be negative, i.e., the current recent average breath period is actually longer than the current interim target period. In such a case, the H(E) function can be made equal to zero if the error is negative so that the pressure will not be changed until the target is increased sufficiently to make the error positive at which time a pressure increase will be called for. However, there are reasons that favor allowing the pressure to be decreased by a negative H(E) if the breathing rate is too slow and the breath period is actually longer than the desired interim target. In certain embodiments, it may not be best to employ a servo-regulation scheme that does not inherently allow the pressure to fall because the overall ventilation of the patient is determined by both patient and ventilator together. So if the patient contributes more effort at the desired rate, or if the ventilatory needs of the patient fall (e.g., transition to a different sleep state), and if the pressure support does not back off, this might possibly result in discomfort and/or arousal. Also, once the optimal rate is achieved, it could be that less pressure support is needed to maintain that rate than was needed to achieve it and for some patients the rate may be depressed too low (below the optimal rate) if the algorithm does not back off. While these patients should perhaps be contraindicated, the issue may be avoided, in certain instances, by allowing the servo control to decrease the pressure as well as increase it.

The approach taken in certain illustrative embodiments is to lower the pressure if the error is negative. However, so that slight lowering of the pressure does not work much against the goal of increasing the breath period, if the recent average rate is lower than the interim target rate (i.e., the error is negative), then the progressive rate target is adjusted to track the patient's recent average rate, that is, the algorithm adopts the slower of the two rates as the next target. Event 3b in FIG. 3A is an example—the interim rate is shifted to the current average rate (i.e., the interim total breath target is made equal to the current average breath interval) because the current recent average rate has fallen below the interim rate. The progressive rate adjustment may not be immediate since it is the recent average rate that is used and not the instantaneous rate, but this is often an acceptable price to pay for allowing pressure changes in both directions.

The interim rate adjustment just described occurs in step 72, which will be described herein. Prior to that, in step 66, the pressure is adjusted up or down as described herein. Then, in step 68, still another test is performed. The error is compared with a threshold value denominated as the hysteresis error. For the moment consider that the threshold value is zero. If the current rate is too high, it means that the error is positive. Since the error is greater than the threshold value, the answer to the test of step 68 is yes. No adjustment is made to the interim target because the breath period is still too short. The pressure will be increased (as a result of step 66) and perhaps now the breath period will lengthen to the period of the interim target. The processing returns to step 50 for another iteration.

If the answer to the test of step 68 is no, it means that things are moving along nicely and the breath period has lengthened to the interim target. Starting in step 70 the various adjustments discussed earlier are made.

Before considering these adjustments, however, it should be noted that the hysteresis error value may be positive instead of zero. This simply means that the answer to the test of step 68 is no even if there is a slight positive error, less than the hysteresis value. The recent average breath period may be a bit too short compared with the current interim value, but it is still treated as having satisfied the interim target so that target values and parameters are adjusted. Hysteresis allows the algorithm to tolerate variation in rate below the interim target without sustained decrement in pressure support. The pressure support will reduce, but perhaps for only one iteration or a few iterations of the loop since a new (lower) target will be adopted.

The test in step 70 checks whether overall success has been achieved. If the interim rate target now in effect is less than the optimal rate target, then the goal has been reached, no changes are necessary and a new iteration begins. But if the interim rate target has not been adjusted all the way to the optimal value, it means that the breathing rate is still faster than optimal, and starting in step 72 adjustments are made in order to slow down the breathing still further. The first adjustment that is made is that described herein—a new interim target period (tgtTtot) is selected. It is the lower of two values. One value is the next value in the progressive target (see FIG. 3A). The other value is the recent average breath period. The longer of the two time interval values is selected. The reason that the recent value may trump the progressive target is that if things are going well, and the patient's breath is slowing down even faster than expected, advantage might as well be taken of the fact.

After the new interim target is selected, it is necessary to set its two individual components, tgtTi and tgtTe since the individual values are needed in step 58. This is done in step 74. As mentioned herein, the two values can be taken from a table or a formula can be used to derive them.

The pressure versus time profile is fixed in the certain illustrative embodiments, but the amplitude and time axes are scaled in step 76 in accordance with the new maximum pressure target PS determined in step 66 and the new interim target period tgtTtot determined in step 72. (See pressure profile at output of turbine 26 on FIG. 2B.)

Referring to FIGS. 6A and 7A, it will be recalled that the cycle threshold plot changes with the progressive Ti target, it being easier to switch to cycling as the target Ti lengthens (i.e., the machine switches to the exhalation mode when the flow intersects the cycle threshold plot at higher values). Using the value of tgtTi determined in step 76, in step 78 the new cycle threshold plot is determined. Similarly, and with reference to FIGS. 8A and 9A and the description herein of how the trigger threshold plot changes with the target Te, in step 80 the value of tgtTe determined in step 76 is used to select the new trigger threshold plot. The processing then continues with a new iteration starting with step 50.

It is inherent in the algorithm or flow chart of FIG. 10 that spontaneous breathing is retained. Once the optimal rate is achieved, pressure support may diminish. Therefore, should the patient be ventilated below his/her apneic threshold during sleep, the triggering/cycling encourage Ti and Te to be maintained at the optimal rate, and pressure support diminished. This will in turn reduce ventilation and ensure the return of spontaneous breathing.

Although the inventions have been described with reference to particular embodiments, it is to be understood that these embodiments are merely illustrative of the application of the principles of the inventions. Thus it is to be understood that numerous modifications may be made in the illustrative embodiments of the inventions and other arrangements may be devised without departing from the spirit and scope of the inventions.

What is claimed is:

1. A method for slowing a patient's breathing by using positive pressure therapy comprising the steps of:
    applying a variable pressure waveform to the patient's airway, setting an interim breathing rate target,
    increasing the magnitude of the variable pressure waveform when the patient's breathing rate is greater than the interim breathing rate target in order to lengthen the patient's breath duration, and
    reducing the interim breathing rate target in response to the patient's breathing rate slowing down toward the interim breathing rate target.

2. The method of claim 1 wherein the variable pressure waveform cycles from an inhalation phase to an exhalation phase when the patient airflow decreases to a cycle threshold, the cycle threshold being (1) a function of flow versus time within a breath and (2) generally increasing with time.

3. The method of claim 2 wherein different interim breathing rate targets have different cycle threshold functions, and the cycle threshold functions allow easier cycling as the interim breathing rate target decreases.

4. The method of claim 1 wherein the variable pressure waveform triggers from an exhalation phase to an inhalation phase when the patient airflow increases to a trigger threshold, the trigger threshold being a function of flow versus time within a breath and generally decreasing with time.

5. The method of claim 4 wherein different interim breathing rate targets have different trigger threshold functions, and the trigger threshold functions allow easier triggering as the interim breathing rate target decreases.

6. The method of claim 1 wherein the magnitude of the variable pressure waveform is decreased if the patient's breathing rate is less than the interim breathing rate target.

7. The method of claim 6 wherein the magnitude of a variable pressure waveform magnitude increase or decrease is a function of the difference between the interim breathing rate target and the patient's breathing rate.

8. A method in accordance with claim 1 wherein the interim breathing rate target is reduced along a predetermined path, but the reduction is paused if the patient's breathing rate is excessively high for the interim breathing rate target.

9. A method in accordance with claim 1 wherein the duration of the variable pressure waveform is adjusted in accordance with the interim breathing rate target.

10. A method for slowing a patient's breathing by using positive pressure therapy comprising the steps of:
    applying a variable pressure waveform to the patient's airway,
    setting an interim breathing rate target,
    increasing the magnitude of the variable pressure waveform that is scaled to the interim breathing rate target if the patient's breathing rate is greater than the interim breathing rate target in order to lengthen the patient's breath duration, the magnitude of the variable pressure waveform magnitude increase being a function of the difference between the interim breathing rate target and the patient's breathing rate, and
    reducing the interim breathing rate target in response to the patient's breathing rate slowing down toward or below the interim breathing rate target.

11. The method of claim 10 wherein said variable pressure waveform cycles from an inhalation phase to an exhalation phase when the patient airflow decreases to a cycle threshold, the cycle threshold being (1) a function of flow versus time within a breath and (2) generally increasing with time.

12. The method of claim 11 wherein different interim breathing rate targets have different cycle threshold functions, and the cycle threshold functions allow easier cycling as the interim breathing rate target decreases.

13. The method of claim 10 wherein the variable pressure waveform triggers from an exhalation phase to an inhalation phase when the patient airflow increases to a trigger threshold, the trigger threshold being a function of flow versus time within a breath and generally decreasing with time.

14. The method of claim 13 wherein different interim breathing rate targets have different trigger threshold functions, and the trigger threshold functions allow easier triggering as the interim breathing rate target decreases.

15. The method of claim 10 wherein said variable pressure waveform cycles from an inhalation phase to an exhalation phase when the patient airflow decreases to a cycle threshold, the cycle threshold being a function of flow versus time within a breath and generally increasing with time, and the variable pressure waveform triggers from an exhalation phase to an inhalation phase when the patient airflow increases to a trigger threshold, the trigger threshold being a function of flow versus time within a breath and generally decreasing with time.

16. The method of claim 15 wherein different interim breathing rate targets have different cycle threshold functions and the cycle threshold functions allow easier cycling as the interim breathing rate target decreases, and different interim breathing rate targets have different trigger threshold functions and the trigger threshold functions allow easier triggering as the interim breathing rate target decreases.

17. A method for slowing a patient's breathing by using a ventilator coupled to a patient's airway comprising the steps of:
    setting an interim breathing rate target,
    increasing the air supplied to the patient's airway from the ventilator during patient breaths if the patient's breathing rate is greater than the interim breathing rate target in order to lengthen the patient's breath duration, reducing the interim breathing rate target in response to the patient's breathing rate slowing down toward the interim breathing rate target, and interrupting the air increase and interim breathing rate target reduction steps if the patient exhibits opposition to breath duration lengthening, the air increase and interim breathing rate target reduction steps being controlled to take place over a period of minutes to hours in the absence of patient opposition.

18. The method of claim 17 wherein the magnitude of an air increase is a function of the difference between the interim breathing rate target and the patient's breathing rate.

19. The method of claim 17 wherein the ventilator is operated so as to synchronize to the patient's breathing rate rather than the interim breathing rate target.

20. The method of claim 17 wherein the ventilator is controlled to cycle from an inhalation phase to an exhalation phase when patient airflow decreases to a cycle threshold, the cycle threshold being (1) a function of flow versus time within a breath and (2) generally increasing with time.

21. The method of claim 20 wherein different interim breathing rate targets have different cycle threshold functions, and the cycle threshold functions allow easier cycling as the interim breathing rate target decreases.

22. The method of claim 17 wherein the ventilator triggers from an exhalation phase to an inhalation phase when patient airflow increases to a trigger threshold, the trigger threshold being a function of flow versus time within a breath and generally decreasing with time.

23. The method of claim 22 wherein different interim breathing rate targets have different trigger threshold functions, and the trigger threshold functions allow easier triggering as the interim breathing rate target decreases.

24. The method of claim 17 wherein the ventilator cycles from an inhalation phase to an exhalation phase when patient airflow decreases to a cycle threshold, the cycle threshold being a function of flow versus time within a breath and generally increasing with time, and the ventilator triggers from an exhalation phase to an inhalation phase when patient airflow increases to a trigger threshold, the trigger threshold being a function of flow versus time within a breath and generally decreasing with time.

25. The method of claim 24 wherein the magnitude of an air increase is a function of the difference between the interim breathing rate target and the patient's breathing rate.

26. The method of claim 24 wherein the ventilator is operated so as to synchronize to the patient's breathing rate rather than the interim breathing rate target.

27. The method of claim 24 wherein different interim breathing rate targets have different cycle threshold functions and the cycle threshold functions allow easier cycling as the interim breathing rate target decreases, and different interim breathing rate targets have different trigger threshold functions and the trigger threshold functions allow easier triggering as the interim breathing rate target decreases.

28. The method of claim 27 wherein the magnitude of an air increase is a function of the difference between the interim breathing rate target and the patient's breathing rate.

29. The method of claim 28 wherein the ventilator is operated so as to synchronize to the patient's breathing rate rather than the interim breathing rate target.

30. The method of claim 27 wherein the ventilator is operated so as to synchronize to the patient's breathing rate rather than the interim breathing rate target.

31. A ventilator for slowing a patient's breathing by using positive pressure therapy comprising:

a blower for applying a variable pressure waveform to the patient's airway, at least one sensor for detecting the breathing rate of the patient, and a controller, wherein the controller is configured to:
set an interim breathing rate target,
cause the blower to increase the magnitude of the variable pressure waveform when the patient's breathing rate is greater than the interim breathing rate target in order to lengthen the patient's breath duration, and
reduce the interim breathing rate target in response to detection of the patient's breathing rate slowing down toward the interim breathing rate target.

32. The ventilator of claim 31 wherein the controller is configured to cause the variable pressure waveform to cycle from an inhalation phase to an exhalation phase when the patient airflow decreases to a cycle threshold, the cycle threshold being (1) a function of flow versus time within a breath and (2) generally increasing with time.

33. The ventilator of claim 32 wherein different interim breathing rate targets have different cycle threshold functions, and the cycle threshold functions allow easier cycling as the interim breathing rate target decreases.

34. The ventilator of claim 31 wherein the controller is configured to cause the variable pressure waveform to trigger from an exhalation phase to an inhalation phase when the patient airflow increases to a trigger threshold, the trigger threshold being a function of flow versus time within a breath and generally decreasing with time.

35. The ventilator of claim 34 wherein different interim breathing rate targets have different trigger threshold functions, and the trigger threshold functions allow easier triggering as the interim breathing rate target decreases.

36. The ventilator of claim 31 wherein the controller is configured to cause the magnitude of the variable pressure waveform to decrease if the patient's breathing rate is less than the interim breathing rate target.

37. The ventilator of claim 36 wherein the controller is configured to cause the magnitude of a variable pressure waveform magnitude increase or decrease to be a function of the difference between the interim breathing rate target and the patient's breathing rate.

38. A ventilator in accordance with claim 31 wherein the controller is configured to cause the interim breathing rate target to be reduced along a predetermined path, but causes the reduction to pause if the patient's breathing rate is excessively high for the interim breathing rate target.

39. A ventilator in accordance with claim 31 wherein the controller is configured to cause the duration of the variable pressure waveform to be adjusted in accordance with the interim breathing rate target.

40. A ventilator for slowing a patient's breathing by using positive pressure therapy comprising:

a blower for applying a variable pressure waveform to the patient's airway, at least one sensor for detecting the breathing rate of the patient, and a controller, wherein the controller is configured to:
set an interim breathing rate target,
cause the blower to increase the magnitude of the variable pressure waveform that is scaled to the interim breathing rate target if the patient's breathing rate is greater than the interim breathing rate target in order to lengthen the patient's breath duration, the magnitude of the variable pressure waveform magnitude increase being a function of the difference between the interim breathing rate target and the patient's breathing rate, and reduce the interim breathing rate target in response to the patient's breathing rate slowing down toward the interim breathing rate target.

41. The ventilator of claim 40 wherein said controller is configured to cause the variable pressure waveform to cycle from an inhalation phase to an exhalation phase when the patient airflow decreases to a cycle threshold, the cycle threshold being (1) a function of flow versus time within a breath and (2) generally increasing with time.

42. The ventilator of claim 41 wherein different interim breathing rate targets have different cycle threshold functions, and the cycle threshold functions allow easier cycling as the interim breathing rate target decreases.

43. The ventilator of claim 40 wherein said controller is configured to cause the variable pressure waveform to trigger from an exhalation phase to an inhalation phase when the patient airflow increases to a trigger threshold, the trigger threshold being a function of flow versus time within a breath and generally decreasing with time.

44. The ventilator of claim 43 wherein different interim breathing rate targets have different trigger threshold functions, and the trigger threshold functions allow easier triggering as the interim breathing rate target decreases.

45. The ventilator of claim 40 wherein said controller is configured to cause the variable pressure waveform to cycle from an inhalation phase to an exhalation phase when the patient airflow decreases to a cycle threshold, the cycle threshold being a function of flow versus time within a breath and generally increasing with time, and said controller causes the variable pressure waveform to trigger from an exhalation phase to an inhalation phase when the patient airflow increases to a trigger threshold, the trigger threshold being a function of flow versus time within a breath and generally decreasing with time.

46. The ventilator of claim 45 wherein different interim breathing rate targets have different cycle threshold functions and the cycle threshold functions allow easier cycling as the interim breathing rate target decreases, and different interim breathing rate targets have different trigger threshold functions and the trigger threshold functions allow easier triggering as the interim breathing rate target decreases.

47. A ventilator for slowing a patient's breathing comprising:
a blower coupled to a patient's airway,
at least one sensor for monitoring the breathing of the patient, and a controller, wherein the controller is configured to:
set an interim breathing rate target,
cause the air supplied to the patient's airway from the blower during patient breaths to increase if the patient's breathing rate is greater than the interim breathing rate target in order to lengthen the patient's breath duration,
reduce the interim breathing rate target in response to the patient's breathing rate slowing down toward the interim breathing rate target, and
interrupt the air increase and interim breathing rate target reduction if the patient exhibits opposition to breath duration lengthening, the controller causing the air increase and interim breathing rate target reduction to take place over a period of minutes to hours in the absence of patient opposition.

48. The ventilator of claim 47 wherein the magnitude of an air increase is a function of the difference between the interim breathing rate target and the patient's breathing rate.

49. The ventilator of claim 47 wherein the controller is configured to cause the blower to operate so as to synchronize it to the patient's breathing rate rather than the interim breathing rate target.

50. The ventilator of claim 47 wherein the controller is configured to cause the blower to cycle from an inhalation phase to an exhalation phase when patient airflow decreases to a cycle threshold, the cycle threshold being (1) a function of flow versus time within a breath and (2) generally increasing with time.

51. The ventilator of claim 50 wherein different interim breathing rate targets have different cycle threshold functions, and the cycle threshold functions allow easier cycling as the interim breathing rate target decreases.

52. The ventilator of claim 47 wherein the controller is configured to cause the blower to trigger from an exhalation phase to an inhalation phase when patient airflow increases to a trigger threshold, the trigger threshold being a function of flow versus time within a breath and generally decreasing with time.

53. The ventilator of claim 52 wherein different interim breathing rate targets have different trigger threshold functions, and the trigger threshold functions allow easier triggering as the interim breathing rate target decreases.

54. The ventilator of claim 47 wherein the controller is configured to cause the blower to cycle from an inhalation phase to an exhalation phase when patient airflow decreases to a cycle threshold, the cycle threshold being a function of flow versus time within a breath and generally increasing with time, and the controller causes the blower to trigger from an exhalation phase to an inhalation phase when patient airflow increases to a trigger threshold, the trigger threshold being a function of flow versus time within a breath and generally decreasing with time.

55. The ventilator of claim 54 wherein the controller is configured to cause the magnitude of an air increase to be a function of the difference between the interim breathing rate target and the patient's breathing rate.

56. The ventilator of claim 54 wherein the controller is configured to cause the blower to operate so as to synchronize to the patient's breathing rate rather than the interim breathing rate target.

57. The ventilator of claim 54 wherein the controller is configured to cause different interim breathing rate targets to have different cycle threshold functions and the cycle threshold functions allow easier cycling as the interim breathing rate target decreases, and the controller causes different interim breathing rate targets to have different trigger threshold functions and the trigger threshold functions allow easier triggering as the interim breathing rate target decreases.

58. The ventilator of claim 57 wherein the controller is configured to cause the magnitude of an air increase to be a function of the difference between the interim breathing rate target and the patient's breathing rate.

59. The ventilator of claim 58 wherein the controller is configured to cause the blower to operate so as to synchronize to the patient's breathing rate rather than the interim breathing rate target.

60. The ventilator of claim 57 wherein the controller is configured to cause the blower to operate so as to synchronize to the patient's breathing rate rather than the interim breathing rate target.

* * * * *